US011643398B2

(12) United States Patent
Lee et al.

(10) Patent No.: US 11,643,398 B2
(45) Date of Patent: May 9, 2023

(54) METALLIC SALT CONTAINING ANION HAVING HETEROCYCLIC AROMATIC STRUCTURE, METHOD OF PREPARING THE METALLIC SALT, AND ELECTROLYTE AND ELECTROCHEMICAL DEVICE EACH INCLUDING THE METALLIC SALT

(71) Applicants: Samsung Electronics Co., Ltd., Suwon-si (KR); Samsung SDI Co., Ltd., Yongin-si (KR)

(72) Inventors: Myungjin Lee, Seoul (KR); Victor Roev, Hwaseong-si (KR); Hongsoo Choi, Seoul (KR); Dongmin Im, Seoul (KR); Yoonhyun Kwak, Seoul (KR); Sangbok Ma, Suwon-si (KR); Minsik Park, Hwaseong-si (KR); Sungjun Park, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 616 days.

(21) Appl. No.: 16/571,332

(22) Filed: Sep. 16, 2019

(65) Prior Publication Data

US 2020/0157058 A1   May 21, 2020

(30) Foreign Application Priority Data

Nov. 15, 2018   (KR) .................. 10-2018-0141125

(51) Int. Cl.
*H01M 10/00*   (2006.01)
*C07D 249/08*   (2006.01)
(Continued)

(52) U.S. Cl.
CPC ......... *C07D 249/08* (2013.01); *C07D 249/18* (2013.01); *C07D 403/04* (2013.01);
(Continued)

(58) Field of Classification Search
CPC ........... H01M 2300/008; H01M 6/164; H01M 10/052; H01M 2300/0034; C07D 249/10
See application file for complete search history.

(56) References Cited

U.S. PATENT DOCUMENTS

| 6,120,696 A | 9/2000 | Armand et al. |
| 6,395,367 B1 | 5/2002 | Michot et al. |

(Continued)

FOREIGN PATENT DOCUMENTS

| EP | 1391952 A2 | 2/2004 |
| EP | 2583337 A1 | 4/2013 |

(Continued)

OTHER PUBLICATIONS

Extended European search report issued by the European Patent Office dated Apr. 28, 2020 in the examination of the European Patent Application No. 19196646.4 which corresponds to the U.S. Appl. No. 16/571,332.

(Continued)

*Primary Examiner* — Cynthia H Kelly
*Assistant Examiner* — Monique M Wills
(74) *Attorney, Agent, or Firm* — Cantor Colburn LLP

(57) ABSTRACT

A metallic salt including at least one anion having a heterocyclic aromatic structure represented by one of Formulae 1 to 3; and a metallic cation:

Formula 1

$$A_1 \underset{\left[X-X\right]_m}{\overset{X^-}{\diagdown\diagup}} A_2$$

(Continued)

-continued

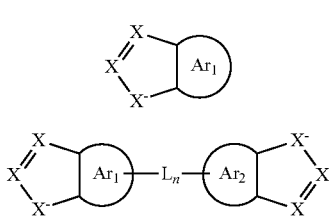

Formula 2

Formula 3 wherein, in Formulae 1 to 3, each X is independently N, P, or As, one of $A_1$ and $A_2$ is an electron-donating group, and the other one is an electron-withdrawing group, ring $Ar_1$ and ring $Ar_2$ are as defined herein, L is a linker group as defined herein, m is an integer from 1 to 5, and n is an integer from 0 to 5.

25 Claims, 6 Drawing Sheets

(51) Int. Cl.
| | |
|---|---|
| C07D 249/18 | (2006.01) |
| C07D 403/04 | (2006.01) |
| C07D 403/14 | (2006.01) |
| H01M 4/1397 | (2010.01) |
| H01M 4/40 | (2006.01) |
| H01M 10/0525 | (2010.01) |
| H01M 10/0568 | (2010.01) |
| H01M 10/0569 | (2010.01) |
| H01M 4/02 | (2006.01) |

(52) U.S. Cl.
CPC ........ *C07D 403/14* (2013.01); *H01M 4/1397* (2013.01); *H01M 4/405* (2013.01); *H01M 10/0525* (2013.01); *H01M 10/0568* (2013.01); *H01M 10/0569* (2013.01); *H01M 2004/028* (2013.01); *H01M 2300/008* (2013.01); *H01M 2300/0034* (2013.01)

(56) References Cited

U.S. PATENT DOCUMENTS

| | | | |
|---|---|---|---|
| 7,513,136 B2 | 4/2009 | Laliberte et al. | |
| 7,745,635 B1 | 6/2010 | Drake | |
| 7,993,782 B2 | 8/2011 | Takada et al. | |
| 8,012,631 B2 | 9/2011 | Seino et al. | |
| 8,075,865 B2 | 12/2011 | Deiseroth et al. | |
| 8,658,317 B2 | 2/2014 | Weppner | |
| 9,452,987 B2 | 9/2016 | Armand et al. | |
| 9,620,811 B2 | 4/2017 | Kambara et al. | |
| 9,728,808 B2 | 8/2017 | Sugiura et al. | |
| 9,812,734 B2 | 11/2017 | Miyashita et al. | |
| 9,929,433 B2 | 3/2018 | Kanno et al. | |
| 2005/0123831 A1 | 6/2005 | Michot et al. | |
| 2006/0068295 A1 | 3/2006 | Xu et al. | |
| 2009/0263725 A1 | 10/2009 | Balsara et al. | |
| 2010/0197813 A1* | 8/2010 | Atwal | A23L 27/204 426/534 |
| 2011/0150736 A1* | 6/2011 | Hagiwara | C07D 233/58 423/276 |
| 2012/0052396 A1 | 3/2012 | Tsuchida et al. | |
| 2012/0118153 A1 | 5/2012 | Omary et al. | |
| 2012/0276434 A1 | 11/2012 | Gaikwad et al. | |
| 2013/0004858 A1 | 1/2013 | Yamada et al. | |
| 2013/0260023 A1 | 10/2013 | Suyama et al. | |
| 2013/0298386 A1 | 11/2013 | Tarascon et al. | |
| 2014/0011100 A1 | 1/2014 | Lee et al. | |
| 2014/0038054 A1 | 2/2014 | Takeshi et al. | |
| 2014/0082931 A1 | 3/2014 | Nishino et al. | |
| 2014/0087270 A1 | 3/2014 | Yoshida | |
| 2014/0162138 A1 | 6/2014 | Fujiki et al. | |
| 2014/0162141 A1 | 6/2014 | Fujiki et al. | |
| 2015/0037688 A1 | 2/2015 | Otsuka et al. | |
| 2015/0093651 A1 | 4/2015 | Aihara et al. | |
| 2015/0118574 A1 | 4/2015 | Visbal et al. | |
| 2015/0147660 A1 | 5/2015 | Fujiki et al. | |
| 2016/0020487 A1 | 1/2016 | Yamada et al. | |
| 2016/0043392 A1 | 2/2016 | Fujiki et al. | |
| 2016/0064772 A1 | 3/2016 | Choi et al. | |
| 2016/0087306 A1 | 3/2016 | Lee et al. | |
| 2016/0093916 A1 | 3/2016 | Moon et al. | |
| 2016/0226097 A1 | 8/2016 | Wegner et al. | |
| 2016/0248093 A1 | 8/2016 | Sugiura et al. | |
| 2017/0047610 A1 | 2/2017 | Miara et al. | |
| 2017/0062829 A1 | 3/2017 | Ryu et al. | |
| 2017/0317352 A1 | 11/2017 | Lee et al. | |
| 2017/0324097 A1 | 11/2017 | Lee et al. | |
| 2018/0226633 A1 | 8/2018 | Fujiki et al. | |
| 2018/0316051 A1 | 11/2018 | Lee et al. | |
| 2019/0044186 A1 | 2/2019 | Kim et al. | |

FOREIGN PATENT DOCUMENTS

| | | |
|---|---|---|
| JP | 2002050345 A | 2/2002 |
| JP | 5066334 B2 | 11/2012 |
| JP | 5224675 B2 | 7/2013 |
| WO | 9829399 A1 | 7/1998 |
| WO | 2013135824 A2 | 9/2013 |

OTHER PUBLICATIONS

Brian D. Adams et al., "Accurate Determination of Coulombic Efficiency for Lithium Metal Anodes and Lithium Metal Batteries," Advanced Energy Materials, Oct. 11, 2017, pp. 1702097 (1-11), vol. 8, Issue 7.

Jennifer Heine et al., "Fluoroethylene Carbonate as Electrolyte Additive in Tetraethylene Glycol Dimethyl Ether Based Electrolytes for Application in Lithium Ion and Lithium Metal Batteries," Journal of the Electrochemical Society, Mar. 24, 2015, pp. A1094-A1101, vol. 162, Issue 6.

\* cited by examiner

METALLIC SALT CONTAINING ANION HAVING HETEROCYCLIC AROMATIC STRUCTURE, METHOD OF PREPARING THE METALLIC SALT, AND ELECTROLYTE AND ELECTROCHEMICAL DEVICE EACH INCLUDING THE METALLIC SALT

CROSS-REFERENCE TO RELATED APPLICATION

This application claims priority to and the benefit of Korean Patent Application No. 10-2018-0141125, filed on Nov. 15, 2018, in the Korean Intellectual Property Office, and all the benefits accruing therefrom under 35 U.S.C. § 119, the disclosure of which is incorporated herein in its entirety by reference.

BACKGROUND

1. Field

The present disclosure relates to metallic salts including an anion having a heterocyclic aromatic structure, methods of preparing the metallic salts, and electrolytes and electrochemical devices each including the metallic salts.

2. Description of the Related Art

As the demand for modern electronic devices increases, energy storage devices that have greater power and energy density while retaining price affordability and safety are required.

Lithium secondary batteries are high-performance secondary batteries having the highest energy density among commercialized secondary batteries. Lithium secondary batteries are electrochemical devices that are used in various fields such as electric vehicles. Lithium secondary batteries may use lithium electrodes as negative electrodes. Lithium electrodes have a large electric capacity per unit weight and thus may realize a higher-capacity battery.

Liquid electrolytes such as carbonate or ether liquid electrolytes having low viscosity are used for lithium metal batteries that use lithium as a negative electrode. In these liquid electrolytes, a porous lithium deposition layer is often formed at a lithium metal interface, and the electrolytes are highly reactive with lithium metal during charging and discharging. In addition, when lithium salts are included in such liquid electrolytes, the anions thereof are electrochemically unstable with respect to the lithium metal of the negative electrode, thereby lowering the efficiency of the lithium negative electrode.

Therefore, there is a continuing need for metallic salts, such as lithium salts, with improved electrochemical stability for use in an electrochemical device.

SUMMARY

Provided are metallic salts which have high electrochemical stability, which leads to improvement of the efficiency and lifetime characteristics of electrochemical devices.

Provided are methods of preparing the metallic salts.

Provided are electrolytes containing the metallic salts.

Provided are electrochemical devices containing the electrolytes that contain the metallic salts.

Additional aspects will be set forth in part in the description which follows and, in part, will be apparent from the description, or may be learned by practice of the presented embodiments.

According to an aspect, a metallic salt includes at least one anion having a heterocyclic aromatic structure represented by one of Formulae 1 to 3; and a metallic cation:

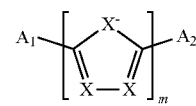

Formula 1

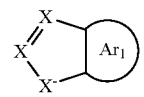

Formula 2

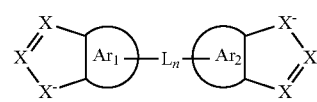

Formula 3

In Formulae 1 to 3, each X may be independently N, P or As, one of $A_1$ and $A_2$ is an electron-donating group (EDG), and the other one is an electron-withdrawing group (EWG), ring $Ar_1$ and ring $Ar_2$ may each independently be an aromatic group that is a substituted or unsubstituted C6 to C24 arylene group or a substituted or unsubstituted C4 to C24 heteroarylene group, wherein the aromatic group may include a single aromatic ring, two or more aromatic rings which are fused together, or two or more aromatic rings which are connected covalently via a single bond, —O—, —S—, —O(=O)—, —S(=O)$_2$—, —Si($R_a$)($R_b$)— (wherein $R_a$ and $R_b$ are each independently a C1 to C10 alkyl group), a substituted or unsubstituted C1 to C10 alkylene group, or —O(=O)—NH—, and wherein $Ar_1$ and $Ar_2$ may each independently be unsubstituted or substituted with at least one of an EDG or an EWG, L is a linker group, and may be a single bond, —O—, —S—, —O(=O)—, —S(=O)$_2$—, —Si($R_a$)($R_b$)— wherein $R_a$ and $R_b$ are each independently a C1 to C10 alkyl group, —O(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker group is unsubstituted or substituted with at least one of an EDG or an EWG, and wherein the linker group L may be non-condensed or condensed with at least one of ring $Ar_1$ or ring $Ar_2$, m may be an integer from 1 to 5, and n may be an integer from 1 to 5.

Another aspect provides an electrolyte including the metallic salt.

Another aspect provides an electrochemical device including the electrolyte.

Another aspect provides a method of preparing a metallic salt, the method including reacting at least one compound having a heterocyclic aromatic structure represented by one of Formulae 1H to 3H and a metallic amide salt to provide the metallic salt, wherein the metallic salt includes a corresponding anion of the heterocyclic aromatic structure:

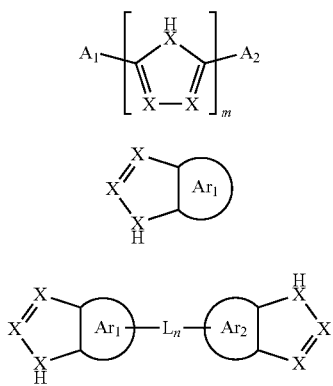

In Formulae 1H to 3H,
each X is independently N, P or As,
one of $A_1$ and $A_2$ is an EDG, and the other one is an EWG,
ring $Ar_1$ and ring $Ar_2$ may each independently be an aromatic group that is a substituted or unsubstituted C6 to C24 arylene group or a substituted or unsubstituted C4 to C24 heteroarylene group, wherein the aromatic group includes a single aromatic ring, two or more aromatic rings which are fused together, or two or more aromatic rings which are covalently connected via a single bond, —O—, —S—, —C(=O)—, —S(=O)$_2$—, —Si($R_a$)($R_b$)— (where $R_a$ and $R_b$ are each independently a C1 to C10 alkyl group), a substituted or unsubstituted C1 to C10 alkylene group, or —C(=O)—NH—, wherein ring $Ar_1$ and ring $Ar_2$ may each independently be unsubstituted or substituted with at least one of an EDG and an EWG,
L is a linker group, and may be a single bond, —O—, —S—, —C(=O)—, —S(=O)$_2$—, —Si($R_a$)($R_b$)— wherein $R_a$ and $R_b$ are each independently a C1 to C10 alkyl group, —C(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker group L is unsubstituted or substituted with at least one of an EDG or an EWG, and wherein the linker group may be uncondensed or condensed with at least one of ring $Ar_1$ or ring $Ar_2$,
m may be an integer from 1 to 5, and
n may be an integer from 1 to 5.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
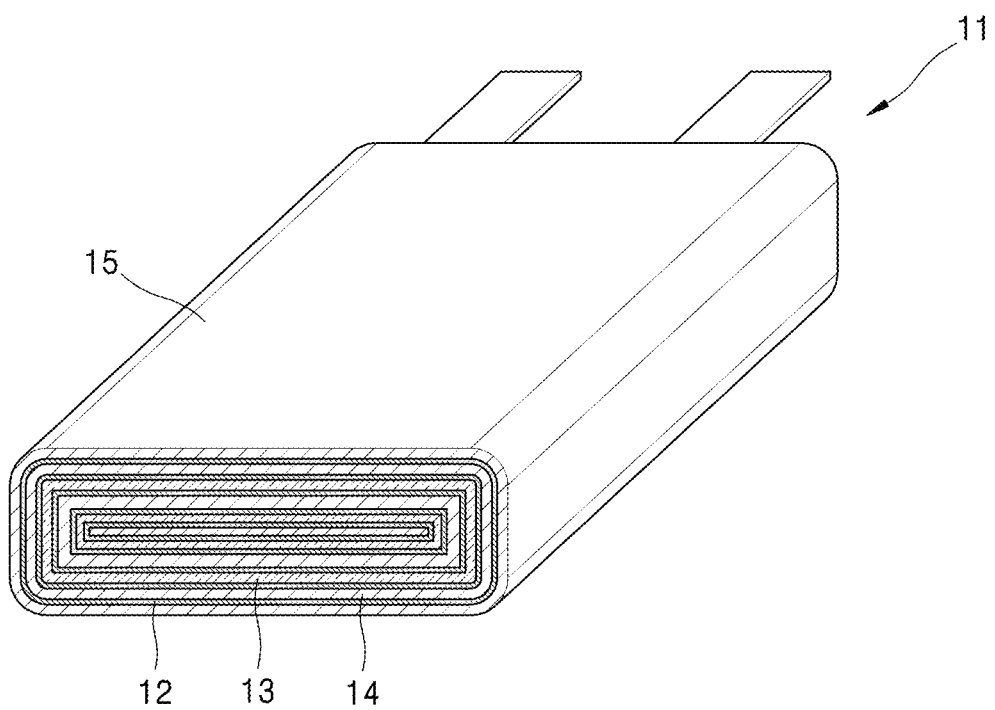
FIG. 1 is a schematic view of a lithium metal battery according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terminology used herein is for the purpose of describing particular examples only and is not intended to limit the present inventive concept. The singular forms "a," "an," and "the" include plural referents unless the context clearly dictates otherwise. Hereinafter, it is to be understood that the terms such as "including," "having," and "comprising" used herein are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. The term "or" means "and/or." The expression "/" may be interpreted as "and" or "or" according to the context.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

In the drawings, the thickness is enlarged or reduced in order to clearly represent layers and regions. Like elements are denoted by like reference numerals throughout the specification. It will be understood that when a layer, a film, a region, or a panel is referred to as being "formed on" another layer, film, region, or panel, it can be directly or indirectly formed on the other layer, film, region, or panel. Throughout the specification, the terms of the first, the second, etc. may be used to describe various components, but the components should not be limited by these terms. These terms are only used to distinguish one component from another. Components having substantially the same functional configuration in the present specification and drawings are denoted by the same reference numerals, and redundant description thereabout will be omitted.

Exemplary embodiments are described hereinafter with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Accordingly, examples of embodiments are illustrated in drawings and will now be described in further detail. It is to be understood, however, that this is not intended to limit the scope present disclosure to any particular embodiment, but is intended to encompass all conversions, equivalents, or alternatives falling within the scope of this disclosure.

Hereinafter a metallic salt having an anion having a heterocyclic aromatic structure according to an embodiment and a method of preparing the metallic salt, an electrolyte including the metallic salt, and an electrochemical device including the metallic salt will be described in further detail.

A metallic salt according to an embodiment includes
at least one anion having a heterocyclic aromatic structure represented by one of Formulae 1 to 3; and
a metallic cation:

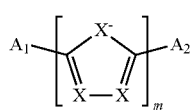

Formula 1

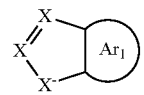

Formula 2

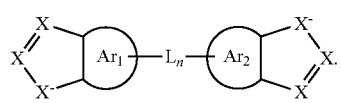

Formula 3

In Formulae 1 to 3,
each X is independently N, P or As,
one of $A_1$ and $A_2$ is an electron-donating group (EDG) and the other one is an electron-withdrawing group (EWG),
ring $Ar_1$ and ring $Ar_2$ may each independently be an aromatic group selected from a substituted or unsubstituted C6 to C24 arylene group or a substituted or unsubstituted C4 to C24 heteroarylene group, wherein the aromatic group may be a single aromatic ring, two or more aromatic rings which are fused together, or two or more aromatic rings which are connected covalently via a single bond, —O—, —S—, —O(=O)—, —S(=O)$_2$—, —Si($R_a$)($R_b$)— (wherein $R_a$ and $R_b$ are each independently a C1 to C10 alkyl group), a substituted or unsubstituted C1 to C10 alkylene group, or —O(=O)—NH—, wherein ring $Ar_1$ and ring $Ar_2$ may each independently be unsubstituted or substituted with at least one selected from an EDG and an EWG;
L is a linker group, and may be a single bond, —O—, —S—, —O(=O)—, —S(=O)$_2$—, —Si($R_a$)($R_b$)— wherein $R_a$ and $R_b$ are each independently a C1 to C10 alkyl group, —O(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker is unsubstituted or substituted with at least one selected from an EDG and an EWG, and wherein the linker group may be non-condensed or condensed with at least one selected from ring $Ar_1$ and ring Are,
m may be an integer from 1 to 5, and
n may be an integer from 1 to 5.

In Formula 1, m may be an integer from 1 to 5. In an embodiment, m may be an integer from 1 to 3. In another embodiment, m may be 1 or 2.

In an embodiment, in Formula 3, L is a linker group, and may be a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker is unsubstituted or substituted with at least one selected from an EDG and an EWG, and the linker may be non-condensed or condensed with at least one selected from ring $Ar_1$ and ring Are.

In another embodiment, L may be a C1-C12 alkylene group, a C2-C12 alkenylene group, a C2-C12 alkynylene group, a C6-C12 arylene group, or a C4-C12 heteroarylene group. In still another embodiment, L may be an aromatic group selected from a C6-C12 arylene group and a C4-C12 heteroarylene group. When L is an aromatic group, non-localization of the non-covalent electrons of the heteroaromatic structure may be increased, leading to an increase in the mobility of Li ions.

In an embodiment, the metallic salt may include an anion having a triazole-based heterocyclic aromatic structure containing three elements of Group 15, wherein the elements are the same or different in the ring structure. A metallic salt having an anion of the heterocyclic aromatic structure with a stable oxidation-reduction potential has excellent oxidation and reduction resistance (i.e., wide electrochemical window) and excellent electrochemical stability. Therefore, the metallic salt is electrochemically stable and may show a high negative electrode efficiency characteristic, with respect to the lithium metal negative electrode, compared with a lithium salt of the prior art contained in a liquid electrolyte. The anion having the heterocyclic aromatic structure may also enhance molecular alignment due to π stacking, and may obtain solubility and planarity at the same time. The planar ring structure of the heterocyclic aromatic structure may reduce anion mobility and may increase Li mobility. As a result, the metallic salt has excellent solubility even in an ether solvent having a relatively small dielectric constant.

Accordingly, when used in various electrochemical devices including lithium secondary batteries, such as a lithium metal battery, or a fuel battery, the metallic salt having an anion having the heterocyclic aromatic structure may provide improved lifespan characteristics.

In an embodiment, the ring $Ar_1$ and ring $Ar_2$ may each independently be selected from the following formulae:

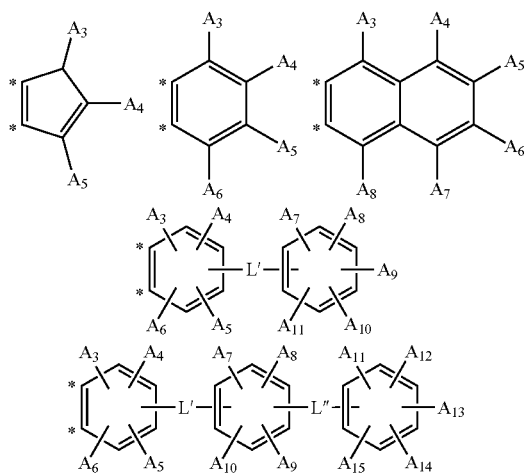

wherein,
$A_3$ to $A_{15}$ may each independently be a hydrogen atom, an EDG, or an EWG;
L' and L" may each be independently a single bond, —O—, —S—, —C(=O)—, —S(=O)$_2$—, —Si($R_a$)($R_b$)— wherein $R_a$ and $R_b$ are each independently a C1 to C10 alkyl group, —C(=O)—NH—, a C1-C12 alkylene group, a C2-C12 alkenylene group, a C2-C12 alkynylene group, a C6-C12 arylene group, or a C4-C12 heteroarylene group, and indicates a binding site to a neighboring atom; and
wherein, for Formula 3, at least one of $A_3$ to $A_{15}$ of ring $Ar_1$ is linked to at least one of $A_3$ to $A_{15}$ of ring $Ar_2$ by the linker group L.

In Formulae 1 to 3, the EDG may be a functional group having electron-donating properties, and the EWG may be a functional group having electron-withdrawing properties. Whether the functional group is the EDG having the electron-donating properties or the EWG having the electron-withdrawing properties may be determined by the person of ordinary skill in the art.

In an embodiment, the EDG has electron-donating properties, and each EDG may be independently a substituted or unsubstituted C1-C30 alkyl group, a substituted or unsubstituted C2-C30 alkenyl group, a substituted or unsubstituted C2-C30 alkynyl group, a substituted or unsubstituted C6-C30 aryl group, a substituted or unsubstituted C1-C30 alkoxy group, a substituted or unsubstituted C2-C30 alkoxyalkyl group, a substituted or unsubstituted C6-C30 aryloxy group, a substituted or unsubstituted C7-C30 aryloxyalkyl group, a substituted or unsubstituted C7-C30 arylalkyl group, a substituted or unsubstituted C2-C30 heteroaryl group, a substituted or unsubstituted C2-C30 heteroaryloxy group, a substituted or unsubstituted C3-C30 heteroarylalkyl group, a substituted or unsubstituted C4-C30 carbocyclic group, a substituted or unsubstituted C5-C30 carbocyclicalkyl group, a substituted or unsubstituted C2-C30 heterocyclic group, a substituted or unsubstituted C3-C30 heterocyclicalkyl group, a substituted or unsubstituted amino group, a substituted or unsubstituted carbamoyl group, a hydroxy group, a nitro group, a cyano group, an amino group, an amidino group, a hydrazine group, a hydrazone group, a carboxyl group or salt thereof, a thiol group, or a phosphoric acid group or salt thereof.

In an embodiment, each EDG may be independently selected from —$C_nH_{2n+1}$, —$OC_nH_{2n+1}$, —$NH_2$, —NH($C_nH_{2n+1}$), —N($C_nH_{2n+1}$)$_2$, —OH, —NH(CO$C_nH_{2n+1}$), —N(CO$C_nH_{2n+1}$)$_2$, —OCO$C_nH_{2n+1}$, —$CH_2$($C_nH_{2n+1}$), —CH($C_nH_{2n+1}$)$_2$, —C($C_nH_{2n+1}$)$_3$, —S$C_nH_{2n+1}$, —N(CH$_2$CH$_2$)$_2$O, —CO$_2$H, —P(O)(OH)$_2$, —P(O)OH, a phenyl group, and a vinyl group, wherein n may be an integer from 1 to 10.

In an embodiment, the EWG may have electron-withdrawing properties, and each EWG may be independently selected from a halogen atom, a cyano group (—CN), an isothiocyanate group (—NCS), a thiocyanate group (—SCN), a cyanato group (—OCN), an isocyanato group (—NCO), a fluorine-substituted C1-C30 alkyl group, a fluorine-substituted C2-C30 alkenyl group, a fluorine-substituted C2-C30 alkynyl group, a fluorine-substituted C6-C30 aryl group, a fluorine-substituted C1-C30 alkoxy group, a fluorine-substituted C2-C30 alkoxyalkyl group, a fluorine-substituted C6-C30 aryloxy group, a fluorine-substituted C7-C30 aryloxyalkyl group, a fluorine-substituted C7-C30 arylalkyl group, a fluorine-substituted C2-C30 heteroaryl group, a fluorine-substituted C2-C30 heteroaryloxy group, a fluorine-substituted C3-C30 heteroarylalkyl group, a fluorine-substituted C4-C30 carbocyclic group, a fluorine-substituted C5-C30 carbocyclicalkyl group, a fluorine-substituted C2-C30 heterocyclic group, a fluorine-substituted C3-C30 heterocyclicalkyl group, a fluorine-substituted thio group, a sulfonyl group, a sulfamoyl group, and a sulfonic acid group or salt thereof.

In an embodiment, each EWG may be independently selected from —F, —Cl, —Br, —CONH$_2$, —COO$C_nH_{2n+1}$, —COCl, —COOH, —CO$C_nH_{2n+1}$, —CHO, —NO$_2$, —SO$_3$H, —C≡N, —S—C≡N, —N=C=S, —N=C=O, —$C_nF_{2n+1}$, —O$C_nF_{2n+1}$, —CH$_2$$C_nF_{2n+1}$, —O$C_nF_{2n+1}$H, —S$C_nF_{2n+1}$, —S$C_nF_{2n}$H, —OCF=CF$_2$, —SCF=CF$_2$, —SO$_2$F, and —SO$_2C_nF_{2n+1}$, wherein n may be an integer from 1 to 10.

In an embodiment, at least one hydrogen atom present in the EDG, the EWG, or both may be substituted with a halogen atom, a C1-C30 alkyl group, a C2-C30 alkenyl group, a C2-C30 alkynyl group, a C1-C30 alkoxy group, a C2-C30 alkoxyalkylene, a C1-C30 heteroalkyl group, a C6-C30 aryl group, a C7-C30 arylalkyl group, a C2-C30 heteroaryl group, a C3-C30 heteroarylalkyl group, a C2-C30 heteroaryloxy group, a C3-C30 heteroaryloxyalkyl group, a C6-C30 heteroarylalkoxy group, a hydroxy group, a nitro group, a cyano group, an amino group, an amidino group, a hydrazine group, a hydrazone group, a carboxyl group or a salt thereof, a sulfonyl group, a sulfamoyl group, a sulfonic acid group or salt thereof, a phosphoric acid group or salt thereof, or a combination thereof.

The heterocyclic aromatic structure may include one monocyclic structure or two or more monocyclic structures connected to each other as illustrated in Formula 1; may have a condensed-cyclic structure as illustrated in Formula 2; condensed-cyclic structures connected via a linker group L as illustrated in Formula 3; or a combination of these structures. The condensed-cyclic structures represented by Formulae 2 and 3 are structures that have not been used as an electrolyte for an electrochemical device, and a functional group combined with an anion may be a hydrogen atom, an EDG, or an EWG. In the case of the monocyclic structure represented by Formula 1, the EDG and the EWG are present at the same time, and the co-presence of the EDG and the EWG has not been used in an electrolyte for an electrochemical device. This structure provides higher lithium negative electrode efficiency than the monocyclic structure having the EWG alone.

In an embodiment, the anion may be a triazole-based anion where each X is nitrogen (N), and may be at least one of the heterocyclic aromatic structures represented by Formulae 1a, 1b, 1c, 2a, 2b, and 3a.

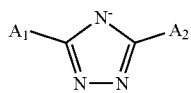

Formula 1a

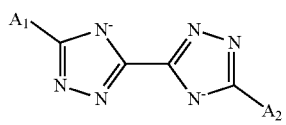

Formula 1b

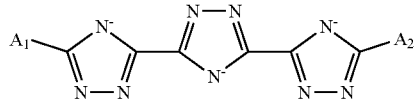

Formula 1c

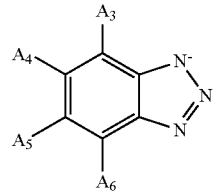

Formula 2a

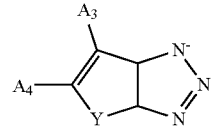

Formula 2b

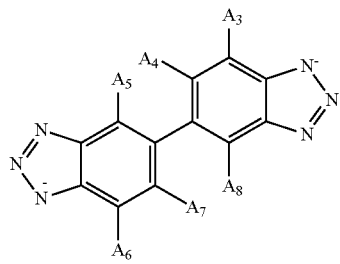

Formula 3a

In Formulae 1a to 3a,
one of $A_1$ and $A_2$ may be an EDG and the other one may be an EWG;
$A_3$ to $A_8$ may each independently be a hydrogen atom, an EDG, or an EWG; and
Y may be a hetero atom, such as oxygen, sulfur, or nitrogen.

The metallic cation of the metallic salt may include at least one selected from $Li^+$, $Na^+$, $K^+$, $Mg^{2+}$, $Ca^{2+}$, $Sm^{3+}$, $La^{3+}$, $Ho^{3+}$, $Sc^{3+}$, $Al^{3+}$, $Y^{3+}$, $Yb^{3+}$, $Lu^{3+}$, and $Eu^{3+}$. The metallic cation may be appropriately selected depending on an electrochemical device and an electrolyte. In an embodiment, the metallic cation may include $Na^+$, $Li^+$, $K^+$, or a combination thereof. For example, the metallic cation may include $Li^+$. The metallic salt may be an alkali metal salt or an alkaline earth metal salt. In an embodiment, the metallic salt may be a lithium salt. Lithium ions have excellent electrochemical properties, and can provide a battery having high-energy density.

The metallic salt may be prepared by reacting a compound having a corresponding heterocyclic aromatic structure and a metallic amide salt as a strong base.

A method of preparing a metallic salt according to an embodiment includes reacting at least one compound having a heterocyclic aromatic structure represented by one of Formulae 1H to 3H and a metallic amide salt to provide the metallic salt, wherein the metallic salt comprises an anion corresponding to the heterocyclic aromatic structure.

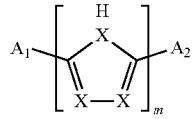

Formula 1H

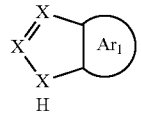

Formula 2H

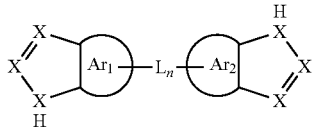

Formula 3H

In Formulae 1H to 3H,
each X is independently N, P or As,
one of $A_1$ and $A_2$ is an EDG, and the other one is an EWG,
ring $Ar_1$ and ring $Ar_2$ may each independently be an aromatic group selected from a substituted or unsubstituted C6 to C24 arylene group or a substituted or unsubstituted C4 to C24 heteroarylene group, wherein the aromatic group may be a single aromatic ring, two or more aromatic rings which are fused together, or two or more aromatic rings which are covalently connected via a single bond, —O—, —S—, —O(=O)—, —S(=O)$_2$—, —Si(R$_a$)(R$_b$)-(wherein R$_a$ and R$_b$ are each independently a C1 to C10 alkyl group), a substituted or unsubstituted C1 to C10 alkylene group, or —O(=O)—NH—, and wherein ring Ar$_1$ and ring Ar$_2$ may each independently be unsubstituted or substituted with at least one selected from an EDG and an EWG, L is a linker group, and may be a single bond, —O—, —S—, —O(=O)—, —S(=O)$_2$—, —Si(R$_a$)(R$_b$)— wherein R$_a$ and R$_b$ are each independently a C1 to C10 alkyl group, —O(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker group L is unsubstituted or substituted with at least one selected from an EDG and an EWG, and wherein the linker group may be non-condensed or condensed with at least one selected ring Ar$_1$ and ring Ar$_2$, m may be an integer from 1 to 5, and n may be an integer from 1 to 5.

The metallic salt containing an anion corresponding to the heterocyclic aromatic structures represented by Formulae 1H to 3H may be the same as described above.

The metallic amide salt is a strong base, and may substitute one or more protons present in the heterocyclic aromatic structures represented by Formulae 1H to 3H with a metallic cation, for example a lithium cation. In the case of the forming the metallic salt corresponding to the heterocyclic aromatic structure by using the metallic amide salt, for example, when converting into a lithium salt, the purity and the lithium substitution degree may be substantially increased compared to when the lithium substitution process using a base such as LiOH or Li$_2$CO$_3$. The purity of the synthesized metallic salt may be measured by using, for example, high-performance liquid chromatography (HPLC, HPLC 2695, waters 2695), and the lithium substitution degree thereof may be measured by using, for example, ion chromatography (IC, ICS5000).

In the case of the metallic salt of Example 1 described below, when the aqueous LiOH solution of the prior art is used, the purity and the lithium substitution degree are 93% and 47%, respectively, while when an lithium diisopropylamide (LDA) salt is used, the purity and the lithium substitution degree are 98.4% and 97%, respectively.

In an embodiment, the metallic amide salt may be a compound represented by Formula 4.

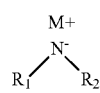

Formula 4 wherein, in Formula 4,

M$^+$ may be at least one metallic cation selected from an alkali metal cation, an alkaline earth metal cation, a transition metal cation, a post-transition metal cation, and a rare-earth metal cation, and R$_1$ and R$_2$ may each independently be a C1-C30 alkyl group, a C2-C30 alkenyl group, a C2-C30 alkynyl group, a C6-C30 aryl group, a C1-C30 alkoxy group, a C2-C30 alkoxyalkyl group, a C6-C30 aryloxy group, a C7-C30 aryloxyalkyl group, a C7-C30 arylalkyl group, a C2-C30 heteroaryl group, a C2-C30 heteroaryloxy group, a C3-C30 heteroarylalkyl group, a C4-C30 carbocyclic group, a C5-C30 carbocyclicalkyl group, a C2-C30 heterocyclic group, a C3-C30 heterocyclicalkyl group, or a C1-C30 silyl group.

In an embodiment, two or more hydrogen atoms present in each of R$_1$ and R$_2$ may be independently substituted with a C1-C30 alkyl group, a C2-C30 alkenyl group, a C2-C30 alkynyl group, a C1-C30 alkoxy group, a C2-C30 alkoxyalkyl group, a C1-C30 heteroalkyl group, a C6-C30 aryl group, a C7-C30 arylalkyl group, a C2-C30 heteroaryl group, a C3-C30 heteroarylalkyl group, a C2-C30 heteroaryloxy group, a C3-C30 heteroaryloxyalkyl group, a C6-C30 heteroarylalkoxy group, a hydroxy group, a nitro group, a cyano group, an amino group, an amidino group, a hydrazine group, a hydrazone group, a carboxyl group or a salt thereof, a sulfonyl group, a sulfamoyl group, a sulfonic acid group or salt thereof, a phosphoric acid group or salt thereof, or a combination thereof.

In an embodiment, the metallic amide salt may include a metallic salt of at least one amide selected from diisopropylamide, hexamethyleneamide, diisobutylamide, t-butylmethylamide, t-butyl-trimethylsilylamide, cyclohexylisopropylamide, cyclohexylmethylamide, allyl-1-phenylethylamide, allyl-(R)-1-phenylethylamide, allyl-(S)-1-phenylethylamide, benzyl-1-phenylethylamide, benzyl-(R)-1-phenylethylamide, benzyl-(S)-1-phenylethylamide, bis-(1-phenylethyl)amide, (+)-bis-[(R)-1-phenylethyl]amide, (−)-bis-[(S)-1-phenylethyl]amide, 2,2,6,6-tetramethylpiperidide, pyrrolidide, piperidide, and bis(trimethylsilyl)amide.

In an embodiment, the metallic amide salt may include lithium diisopropylamide, lithium bis(trimethylsilyl)amide, or a combination thereof.

In an embodiment, the converting process may be performed under an inert atmosphere. For example, the converting process may be carried out under an inert atmosphere including argon, nitrogen or a combination thereof. For example, the inert atmosphere may contain less than 10 parts per million (ppm) of oxygen. Optionally, the inert atmosphere may be free of water, for example less than 10 ppm of water. Under the inert atmosphere, a high purity and a high metal substitution degree may be obtained.

In an embodiment, the converting process may be carried out at a temperature equal to or below 0° C. When the reaction is carried out at a temperature of 0° C. or lower, a side reaction, for example, the substitution of lithium at an undesired position may be prevented.

According to another embodiment, there is provided an electrolyte for an electrochemical device including the metallic salt described above.

The electrolyte may be a liquid electrolyte, a gel electrolyte, a solid electrolyte, a polymeric ionic liquid, or a combination thereof, wherein the metallic salt may be included in at least one selected from the liquid electrolyte, the gel electrolyte, the solid electrolyte, and the polymeric ionic liquid.

In an embodiment, the electrolyte may be a liquid electrolyte. The liquid electrolyte may include the metallic salt and an organic solvent.

In a liquid electrolyte, the organic solvent may include a low-boiling point solvent. The low-boiling point solvent as used herein means a solvent having a boiling point of 200° C. or lower at 1 atm.

In an embodiment, the organic solvent may include at least one selected from dialkyl carbonates, cyclic carbonates, linear or cyclic esters, linear or cyclic amides, aliphatic nitriles, sulfone compounds, linear or cyclic ethers, and derivatives thereof.

The organic solvent may include at least one selected from dimethyl carbonate (DMC), diethyl carbonate (DEC), ethylmethyl carbonate (EMC), methylpropyl carbonate, ethylpropyl carbonate, methylisopropyl carbonate, dipropyl carbonate, dibutyl carbonate, propylene carbonate (PC), ethylene carbonate (EC), fluoroethylene carbonate (FEC), butylene carbonate, diethylene glycol dimethylether, triethylene glycol dimethylether, tetraethylene glycol dimethylether, polyethylene glycol dimethylether, dimethyl sulfone, ethylmethyl sulfone, diethyl sulfone, adiponitrile, 1,1,2,2-tetrafluoroethyl-2,2,3,3-tetrafluoropropyl ether, ethylpropionate, ethylbutyrate, benzonitrile, acetonitrile, tetrahydrofuran, 2-methyltetrahydrofuran, gamma-valerolactone, gamma-butyrolactone, succinonitrile (SN), N-methyl-2-pyrrolidinone, dioxolane, 4-methyldioxolane, N,N-dimethylformamide, N,N-dimethylacetamide, dimethyl sulfoxide, dioxane, sulfolane, dichloroethane, chlorobenzene, and nitrobenzene, but is not limited thereto. Any organic solvent available in the art may be used in the organic solvent.

In an embodiment, the amount of the metallic salt in the liquid electrolyte may range from about 0.1 moles per liter (M) to about 7 M based on the organic solvent. For example, the amount of the metallic salt may range from 0.5 M to 5 M based on the organic solvent. For example, the amount of the metallic salt may range from 1 M to 3 M based on the organic solvent. When the amount of the metallic salt is within the above ranges, the electrolyte may provide excellent lifetime characteristics improvement effects to an electrochemical battery without increasing the internal resistance.

To improve charging and discharging characteristics or flame retardancy, the liquid electrolyte may include, for example, pyridine, triethylphosphite, triethanolamine, a cyclic ether, ethylenediamine, n-glyme, hexamethylphosphoramide, a nitrobenzene derivative, sulfur, a quinone imine dye, an N-substituted oxazolidinone, an N,N-substituted imidazolidine, ethylene glycol dialkyl ethers, ammonium salts, pyrrole, 2-methoxyethanol, aluminum trichloride, or the like. In an embodiment, halogen-containing solvents such as carbon tetrachloride and ethylene trifluoride may be further added to provide nonflammability.

In an embodiment, the liquid electrolyte may further include an ionic liquid. The ionic liquid may be any that is commonly used in the manufacture of electrolytes in the art.

The ionic liquid may include, for example, i) at least one cation selected from ammoniums, pyrrolidiniums, pyridiniums, pyrimidiniums, imidazoliums, piperidiniums, pyrazoliums, oxazoliums, pyridaziniums, phosphoniums, sulfoniums, and triazoliums, and ii) an anion.

The anion may include at least one selected from, for example, $BF_4^-$, $PF_6^-$, $AsF_6^-$, $SbF_6^-$, $AlCl_4^-$, $HSO_4^-$, $ClO_4^-$, $CH_3SO_3^-$, $CF_3CO_2^-$, $(CF_3SO_2)_2N^-$, $(FSO_2)_2N^-$, $Cl^-$, $Br^-$, $I^-$, $SO_4^{2-}$, $CF_3SO_3^-$, $(C_2F_5SO_2)_2N^-$, $(C_2F_5SO_2)(CF_3SO_2)N^-$, $NO_3^-$, $Al_2Cl_7^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$, but is not limited thereto.

In an embodiment, the liquid electrolyte may further include lithium salts that are commonly used in the manufacture of electrolytes in the art. Examples of the lithium salt include LiSCN, $LiN(CN)_2$, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiSbF_6$, $Li(FSO_2)_2N$, $LiC_4F_9SO_3$, $LiN(SO_2CF_2CF_3)_2$, $LiSbF_6$, $LiPF_3(C_2F_5)_3$, $LiPF_3(CF_3)_3$, LiCl, LiF, LiBr, LiI, $LiB(C_2O_4)_2$ (lithium (bis(oxalato)borate, LiBOB), lithium difluoro(oxalato)borate (LiFOB), or a combination thereof.

According to an embodiment, the lithium salt may be a fluorine-containing sulfonyl compound. The fluorine-containing sulfonyl compound may be $LiN(FSO_2)_2$ (LiFSI), $LiN(CF_3SO_2)_2$ (LiTFSI), $LiN(CF_3SO_2)$ $(CF_3CF_2CF_2CF_2SO_2)$, $LiN(CF_3CF_2SO_2)_2$, $LiC(CF_3SO_2)_2$, or $LiC(CF_3CF_2SO_2)_2$.

When a lithium salt available in the art is additionally used, the total amount of the lithium salt and the metallic salt may be in the range of about 0.1 M to about 7 M based on the total amount of the liquid electrolyte. Even when the lithium salt is added, when the total amount of the lithium salt and the metallic salt is in the above range, the lifespan characteristic of the electrochemical cell is improved without increasing the internal resistance.

The liquid electrolyte may have the viscosity of, for example, 5 centipoise (cP) or less, for example, about 2.5 cP to about 4.0 cP, at a temperature of 25° C. When the viscosity of the liquid electrolyte is within the above range, an electrochemical device having excellent electrolyte conductivity and oxidation resistance and improved high voltage stability may be obtained.

The ionic conductivity of the liquid electrolyte may be 1.0 milliSiemens per centimeter (mS/cm) or more, for example, about 1 mS/cm to about 5 mS/cm, at a temperature of 25° C.

The gel electrolyte may be an electrolyte having a gel form that contains components and shape known in the art.

The gel electrolyte may contain, for example, polymers and polymeric ionic liquids.

The polymer may be, for example, a solid graft (block) copolymer.

The solid electrolyte may be an organic solid electrolyte, an inorganic solid electrolyte, or a combination thereof.

The organic solid electrolyte may be, for example, a polyethylene derivative, a polyethylene oxide derivative, polypropylene oxide derivative, phosphoric acid ester polymer, polyglyceride lysine, poly ester sulfide, polyvinyl alcohol, polyvinylidene fluoride, or a polymer including an ionic dissociation group.

The inorganic solid electrolyte may be $Cu_3N$, $Li_3N$, LiPON, $Li_3PO_4$—$Li_2S$—$SiS_2$, $Li_2S$—$GeS_2$—$Ga_2S_3$, $(Na, Li)_{1+x}Ti_{2-x}Al_x(PO_4)_3$ (wherein $0.1 \leq x \leq 0.9$), $Li_{1-x}Hf_{2-x}Al_x(PO_4)_3$ (wherein $0.1 \leq x \leq 0.9$), $Na_3Zr_2Si_2PO_{12}$, $Li_3Zr_2Si_2PO_{12}$, $Na_5ZrP_3O_{12}$, $Na_5TiP_3O_{12}$, $Na_3Fe_2P_3O_{12}$, $Na_4NbP_3O_{12}$, $NLi_{0.3}La_{0.5}TiO_3$, $Na_5MSi_4O_{12}$ (wherein M may be a rare earth element, such as Nd, Gd, or Dy), $Li_5ZrP_3O_{12}$, $Li_5TiP_3O_{12}$, $Li_3Fe_2P_3O_{12}$, $Li_4NbP_3O_{12}$, $Li_{1+x}(M,Al,Ga)_x(Ge_{1-y}Ti_y)_{2-x}(PO_4)_3$ (wherein $0 \leq x \leq 0.8$, $0 \leq y \leq 1.0$, and wherein M may be Nd, Sm, Eu, Gd, Tb, Dy, Ho, Er, Tm, or Yb), $Li_{1+x+y}Q_xTi_{2-x}Si_yP_{3-y}O_{12}$ (wherein $0 < x \leq 0.4$, $0 < y \leq 0.6$, and wherein Q is Al or Ga), $Li_6BaLa_2Ta_2O_{12}$, $Li_7La_3Zr_2O_{12}$, $Li_5La_3Nb_2O_{12}$, $Li_5La_3M_2O_{12}$ (wherein M is Nb or Ta), $Li_{7+x}A_xLa_{3-x}Zr_2O_{12}$ (wherein $0 < x < 3$, where A is Zn), or the like.

The polymeric ionic liquid may be obtained, for example, by polymerizing ionic liquid monomers, or may be a polymeric compound. These polymeric ionic liquids have a high solubility with respect to an organic solvent, and when added to an electrolyte, may improve the ionic conductivity.

When the polymeric ionic liquid is obtained by polymerizing ionic liquid monomers, the polymerization reaction product is washed and dried, and then an anion substitution reaction is carried out thereon so as to have an appropriate anion capable of providing a solubility with respect to an organic solvent.

The polymeric ionic liquid according to an embodiment may include a repeating unit including i) at least one cation selected from ammoniums, pyrrolidiniums, pyridiniums, pyrimidiniums, imidazoliums, piperidiniums, pyrazoliums, oxazoliums, pyridaziniums, phosphoniums, sulfoniums, triazoliums, and mixtures thereof, and ii) at least one anion selected from $BF_4^-$, $PF_6^-$, $AsF_6^-$, $SbF_6^-$, $AlCl_4^-$, $HSO^{4-}$, $CH_3SO_3^-$, $CF_3CO_2^-$, $(CF_3SO_2)_2N^-$, $Cl^-$, $Br^-$, $I^-$, $SO_4^{2-}$, $CF_3SO_3^-$, $(C_2F_5SO_2)_2N^-$, $(C_2F_5SO_2)(CF_3SO_2)N^-$, $NO_3^-$, $Al_2Cl_7^-$, $CH_3COO^-$, $(CF_3SO_2)_3C^-$, $(CF_3)_2PF_4^-$, $(CF_3)_3PF_3^-$, $(CF_3)_4PF_2^-$, $(CF_3)_5PF^-$, $(CF_3)_6P^-$, $SF_5CF_2SO_3^-$, $SF_5CHFCF_2SO_3^-$, $CF_3CF_2(CF_3)_2CO^-$, $(CF_3SO_2)_2CH^-$, $(SF_5)_3C^-$, and $(O(CF_3)_2C_2(CF_3)_2O)_2PO^-$.

In an embodiment, a polymeric ionic liquid may be prepared by polymerizing ionic liquid monomers. The ionic liquid monomer has a polymerizable functional group such as a vinyl group, an allyl group, an acrylate group, a methacrylate group, and the like, and at least one cation selected from ammoniums, pyrrolidiniums, pyridiniums, pyrimidiniums, imidazoliums, piperidiniums, pyrazoliums, oxazoliums, pyridaziniums, phosphoniums, sulfoniums, triazoliums, and mixtures thereof and the anion described above.

Examples of the ionic liquid monomer include 1-vinyl-3-ethyl imidazolium bromide and a compound represented by Formula 5 or 6.

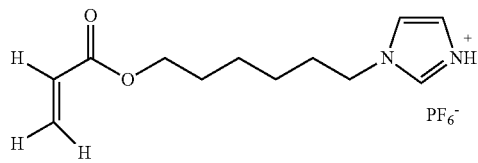

Formula 5

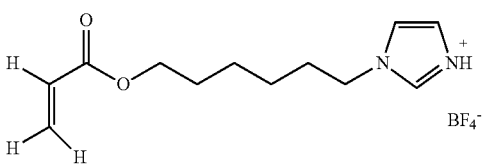

Formula 6

Examples of the above polymeric ionic liquid include a compound represented by Formula 7 or a compound represented by Formula 8.

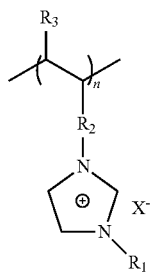

Formula 7

In Formula 7, $R_1$ and $R_3$ may each independently be hydrogen, a substituted or unsubstituted C1-C30 alkyl group, a substituted or unsubstituted C2-C30 alkenyl group, a substituted or unsubstituted C2-C30 alkynyl group, a substituted or unsubstituted C6-C30 aryl group, a substituted or unsubstituted C2-C30 heteroaryl group, or a substituted or unsubstituted C4-C30 carbocyclic group.

$R_2$ indicates a single bond, or a C1-C30 alkylene group, a C6-C30 arylene group, a C2-C30 heteroarylene group, or a divalent C4-C30 carbocyclic group, $X^-$ represents an anion of the ionic liquid, and n may be in the range of 500 to 2800.

Formula 8 has the following structure:

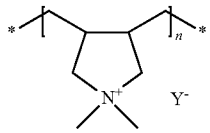

Formula 8

In Formula 8, $Y^-$ is defined in the same manner as $X^-$ of Formula 7, and n may be in the range of 500 to 2800.

For example, $Y^-$ in Formula 8 may be bis(trifluoromethanesulfonyl)imide (TFSI), $BF_4^-$, or $CF_3SO_3^-$.

The polymeric ionic liquid may include, for example, a cation selected from poly(1-vinyl-3-alkylimidazolium), poly(1-allyl-3-alkylimidazolium), poly(1-(methacryloyloxy)-3-alkyl imidazolium); and an anion selected from $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F_7COO^-$, and $(CF_3SO_2)(CF_3CO)N^-$.

A compound represented by Formula 8 may be a polydiallyldimethylammonium bis(trifluoromethanesulfonyl)imide.

In an embodiment, a polymeric ionic liquid may include a low molecular weight polymer, a thermally stable ionic liquid, and a lithium salt. The low molecular weight polymer may have an ethylene oxide polymer chain. The low molecular weight polymer may be a glyme. Glyme used herein refers to, for example, polyethylene glycol dimethyl ether (polyglyme), tetraethylene glycol dimethyl ether (tetraglyme), and triethylene glycol dimethylether (triglyme).

The weight average molecular weight of the low molecular weight polymer may be from about 75 to about 2000 gram per mole (g/mol), for example, about 250 to about 500 g/mol.

According to another embodiment, there is provided an electrochemical device including the electrolyte described above. The electrochemical device may include a lithium battery, a fuel cell, a supercapacitor, or the like.

A lithium battery according to an embodiment includes: a positive electrode; a negative electrode; and an electrolyte disposed between the positive electrode and the negative electrode, wherein the electrolyte includes the metallic salts as described above.

The negative electrode may include a negative active material. The negative electrode may be manufactured as follows: a negative active material, a binder, a conductive agent, which is optional, and a solvent are mixed to prepare a negative active material composition, which is then molded into a given shape or coated on a copper foil.

The negative active material may be any material that is used in the art. The non-limiting examples of the negative active material may be lithium metal, a lithium-alloyable metal, a transition metal oxide, a material capable of doping and dedoping lithium, or a material capable of reversibly intercalating and deintercalating lithium ions. Two or more of these may be mixed or bonded together for use.

Non-limiting examples of the transition metal oxides may be tungsten oxide, molybdenum oxide, titanium oxide, lithium titanium oxide, vanadium oxide, lithium vanadium oxide, and the like.

The material capable of doping and dedoping lithium may be, for example, Si, $SiO_x$ (wherein $0 \leq x \leq 2$), Si—Y' alloy (wherein Y' is alkali metal, alkali earth metal, a Group 13 element, a Group 14 element, a Group 15 element, a Group 16 element, a transition metal, rare earth element, or a combination thereof, provided that Y' is not Si), Sn, $SnO_2$, or Sn—Y" alloy (wherein Y" is alkali metal, alkali earth metal, a Group 13 element, a Group 14 element, a Group 15 element, a Group 16 element, transition metal, rare earth element, or a combination thereof, provided that Y" is not Sn), and at least one of these may be mixed with $SiO_2$ for use. The element Y' or Y" may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, Po, or a combination thereof.

The material capable of reversibly intercalating and deintercalating lithium ions may be a carbonaceous material, for example, any carbonaceous negative active material that is commonly used in a lithium battery. In an embodiment, the carbonaceous material may be a crystalline carbon, an amorphous carbon, or a mixture thereof. Non-limiting examples of the crystalline carbon are natural graphite that is non-shaped, tabular, flake, spherical, or fibrous; or artificial graphite. Non-limiting examples of the amorphous carbon include soft carbon, hard carbon, mesophase pitch carbonization product, calcinated coke, and the like.

In an embodiment, the negative active material may be an active material that embodies a high capacity, and examples of such a material are a silicon active material, such as Si, $SiO_x$ (wherein $0 \leq x \leq 2$), or Si—Y' alloy, a tin active material, such as Sn, $SnO_2$, or Sn—Y" alloy, a silicon-tin alloy active material, and a silicon-carbon active material.

In the case of the active material that embodies a high capacity, even during swelling or shrinking of an active material due to charging and discharging, an aqueous binder binding between active materials may prevent the release of the active material and maintains an electron delivery path inside an electrode, thereby improving the rate characteristics of a lithium battery.

The negative active material may further include a carbonaceous negative active material, in addition to the silicon active material, the tin active material, the silicon-tin alloy-active material, the silicon-carbon active material, or a combination thereof. The carbonaceous negative active material may form a mixture or composite with the silicon active material, the tin active material, the silicon-tin alloy active material, the silicon-carbon active material, or the combination thereof.

The negative active material may have a simple particle shape, and may be a nano structure having the nano magnitude. For example, the negative active material may have a variety of forms, including nanoparticles, nanowires, nanorods, nanotubes, and nanobelts.

In an embodiment, the binder used in the negative active material composition may include a water-soluble polyamic acid, and due to the inclusion thereof, the volumetric expansion of the negative active material that may occur during charging and discharging of lithium may be prevented. The binder containing the water-soluble polyamic acid may be added in an amount of about 1 part by weight to about 20 parts by weight, for example, about 2 parts by weight, to about 10 parts by weight, based on 100 parts by weight of the negative active material.

The negative electrode may further optionally include a conductive agent to improve electrical conductivity. The conductive agent may be any material that is used for a lithium battery in the art, and examples thereof are carbonaceous materials, such as carbon black, acetylene black, Ketjen black, or carbon fiber (for example, vapor-grown carbon fiber); metal-based materials such as metal powders or metal fibers, such as copper, nickel, aluminum, and silver; conductive polymers such as a polyphenylene derivative; or a mixture thereof The amount of the conductive agent may be appropriately adjusted.

As the solvent, N-methylpyrrolidone (NMP), acetone, water and the like may be used. The amount of solvent used may be in the range of about 10 to about 300 parts by weight based on 100 parts by weight of the negative active material. When the amount of the solvent is within the above range, the active material layer may be easily prepared.

The negative active material composition may include other additives, examples which are an adhesion improving agent, such as a silane coupling agent, for improving adhesion of a current collector with respect to an active material, and a dispersant for improving dispersibility of slurry.

The current collector may have a thickness of about 3 micrometers (μm) to about 100 μm. The current collector may be any that has conductivity while not causing a chemical change in a corresponding battery, and examples of the current collector are copper, stainless steel, aluminum, nickel, titanium, calcined carbon; copper and stainless steel, surface-treated with carbon, nickel, titanium, silver, or the like; and an aluminum-cadmium alloy. In one embodiment, fine uneven structures may be formed on the surface of the negative electrode current collector to enhance the bonding force of the negative active material, and the negative electrode current collector may be used in various forms such as a film, a sheet, a foil, a net, a porous body, a foam, or a nonwoven fabric.

The negative active material composition may be directly coated on the current collector to produce a negative electrode plate, or may be cast onto a separate support and a negative active material film exfoliated from the support is laminated on a copper current collector, thereby obtaining a negative electrode plate. The negative electrode is not limited to those described above, but may be of other forms.

In an embodiment, the negative electrode may be a lithium negative electrode.

The lithium negative electrode may be a lithium metal electrode or a lithium alloy electrode.

The lithium alloy may include lithium and a metal/metalloid capable of alloying with lithium. In an embodiment, the lithium-alloyable metal/metalloid may be Si, Sn, Al, Ge, Pb, Bi, Sb, Si—Y' alloy (wherein Y' is alkali metal, alkali earth metal, a Group 13 element, a Group 14 element, a Group 15 element, a Group 16 element, transition metal, rare earth element, or a combination thereof, provided that Y' is not Si), or Sn—Y" alloy (wherein Y" is alkali metal, alkali earth metal, a Group 13 element, a Group 14 element, a Group 15 element, a Group 16 element, transition metal, rare earth element, or a combination thereof, provided that Y" is not Sn). The element Y' or Y" may be Mg, Ca, Sr, Ba, $R_a$, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, Po, or a combination thereof.

For a lithium metal battery including the lithium negative electrode, stability thereof may be excellent even at a high voltage of 4.35 V or higher, for example, around 4.4 V to around 4.5 V.

Apart from the negative electrode, provided is a positive active material composition in which a positive active material, a conductive agent, a binder, and a solvent are mixed.

As the positive active material, a compound capable of reversible intercalation and deintercalation of lithium (a lithiated intercalation compound) may be used. The positive active material may be any lithium-containing material that is used in the art. The positive active material may be represented by any one of the following formulae: $Li_aA_{1-b}B'_bD_2$ (where $0.90 \leq a \leq 1.8$, and $0 \leq b \leq 0.5$), $Li^aE_{1-b}B'b_{2-c}D_c$ (where $0.90 \leq a \leq 1.8$, $0 \leq b \leq 0.5$), $0 \leq c \leq 0.05$); $LiE_{2-b}B'_bO_{4-c}D_c$ (where $0 \leq b \leq 0.5$ and $0 \leq c \leq 0.05$), $Li_aN_{1-b-c}Co_bB'_cD_\alpha$ (where $0.90 \leq a \leq 1.8$, $0 \leq c \leq 0.05$, and $0 < \alpha \leq 2$), $Li_aNi_{1-b-c}Co_bB'_cO_{2-\alpha}F_\alpha$ (where $0.90 \leq a \leq 1.8$, $0 \leq b \leq 0.5$, $0 \leq c \leq 0.05$, and $0 < \alpha < 2$); $Li_aNi_{1-b-c}Mn_bB'_cD_\alpha$ (where $0.90 \leq a \leq 1.8$, $0 \leq b \leq 0.5$, $0 \leq c \leq 0.05$, and $0 < \alpha < 2$), $Li_aNi_{1-b-c}Mn_bB'_cO_{2-\alpha}F_\alpha$ (where $0.90 \leq a \leq 1.8$, $0 \leq b \leq 0.5$, $0 \leq c \leq 0.05$, and $0 < \alpha < 2$); $Li_aNi_bE_cG_dO_2$ (where $0.90 \leq a \leq 1.8$, $0 \leq b \leq 0.9$, $0 \leq c \leq 0.05$, and; $0.001 \leq d \leq 0.1$); $Li_aNi_bCo_cMn_d G_eO_2$ (where $0.90 \leq a \leq 1.8$, $0 \leq b \leq 0.9$, $0 \leq c \leq 0.5$, $0 \leq d \leq 0.5$, and $0.001 \leq e \leq 0.1$), $Li_aNiG_bO_2$ (where $0.90 \leq a \leq 1.8$ and $0.001 \leq b \leq 0.1$), $Li_aCoG_bO_2$ (where $0.90 \leq a \leq 1.8$ and $0.001 \leq b \leq 0.1$); $Li_aMnG_bO_2$ (where $0.90 \leq a \leq 1.8$ and $0.001 \leq b \leq 0.1$); $Li_aMn_2G_bO_4$ (where $0.90 \leq a \leq 1.8$, and $0.001 \leq b \leq 0.1$); $QO_2$; $QS_2$; $LiQS_2$; $V_2O_5$; $LiV_2O_5$; $LiI'O_2$; $LiNiVO_4$; $Li_{(3-f)}J_2(PO_4)_3$ (where $0 \leq f \leq 2$); $Li_{(3-f)}Fe_2(PO_4)_3$ (where $0 \leq f \leq 2$); and $LiFePO_4$.

In the chemical formulae above, A is Ni, Co, Mn, or a combination thereof; B' is Al, Ni, Co, Mn, Cr, Fe, Mg, Sr, V, a rare-earth element, or a combination thereof; D is O, F, S, P, or a combination thereof; E is Co, Mn, or a combination thereof; F is F, S, P, or a combination thereof; G is Al, Cr, Mn, Fe, Mg, La, Ce, Sr, V, or a combination thereof; Q is Ti, Mo, Mn, or a combination thereof; I' is Cr, V, Fe, Sc, Y, or a combination thereof; and J is V, Cr, Mn, Co, Ni, Cu, or a combination thereof.

The positive active material may include, for example, at least one selected from lithium cobalt oxide, such as $LiCoO_2$; lithium nickel oxide, such as $LiNiO_2$; lithium manganese oxide, such as $Li_{1+x}Mn_{2-x}O_4$ (where x may be in the range of 0 to 0.33), $LiMnO_3$, $LiMn_2O_3$, or $LiMnO_2$; lithium copper oxide, such as $Li_2CuO_2$; lithium iron oxide, such as $LiFe_3O_4$; lithium vanadium oxide, such as $LiV_3O_8$; copper vanadium oxide, such as $Cu_2V_2O_7$; vanadium oxide, such as $V_2O_5$; lithium nickel composite oxide, such as $LiNi_{1-x}M_xO_2$ (where M=Co, Mn, Al, Cu, Fe, Mg, B, or Ga, and x is 0.01 to 0.3); lithium manganese composite oxide, such as $LiMn_{2-x}M_xO_2$ (where M=Co, Ni, Fe, Cr, Zn, or Ta, and x is 0.01 to 0.1) or $Li_2Mn_3MO$ (where M=Fe, Co, Ni, Cu, or Zn); lithium manganese oxide, such as $LiMn_2O_4$ wherein some Li are substituted with an alkali earth metal ion; a disulfide compound; and iron molybdenum oxide, such as $Fe_2(MoO_4)_3$.

For use as the positive active material, an active material core that is surface-coated with a coating may be used. The coating layer may include a coating element compound, such as an oxide of a coating element, a hydroxide of a coating element, an oxyhydroxide of a coating element, an oxycarbonate of a coating element, or a hydroxycarbonate of a coating element. Compounds forming these coating layers may be amorphous or crystalline. As a coating element included in a coating layer, at least one of Mg, Al, Co, K, Na, Ca, Si, Ti, V, Sn, Ge, Ga, B, As, and Zr may be used. The process for forming a coating layer may be performed by using any method that does not adversely affect properties of a positive active material while using these compounds and these elements (for example, spray coating, immersing, or the like). For example, $LiNiO_2$, $LiCoO_2$, $LiMn_xO_{2x}$ (x=1, 2), $LiNi_{1-x}Mn_xO_2$ ($0<x<1$), $LiNi_{1-x-y}Co_xMn_yO_2$ ($0 \leq x \leq 0.5$, $0 \leq y \leq 0.5$), $LiFeO_2$, $V_2O_5$, TiS, or MoS may be used.

The binder for the positive active material composition may be any material that allows positive active material particles to attach on each other and also attaches a positive active material on a current collector. The binder may include one or more selected from polyvinyl alcohol, carboxymethylcellulose, hydroxypropylcellulose, diacetylcellulose, polyvinyl chloride, carboxylated polyvinyl chloride, polyvinyl fluoride, a polymer containing ethylene oxide, polyvinyl pyrrolidone, polyurethane, polytetrafluoroethylene, polyvinylidene fluoride, polyethylene, polypropylene, styrene-butadiene rubber, polyamideimide, acrylated styrene-butadiene rubber, epoxy resin, and nylon.

The binder used in the positive active material composition may be the same as used in the negative active material composition.

The conductive agent and the solvent for use in the positive active material composition may be the same as used in the negative active material. In some cases, a plasticizer may be further added to the positive active material composition and the negative active material composition to form pores inside an electrode plate. The amounts of the positive active material, the conductive agent, the binder, and the solvent used for the positive active material composition are at the same levels as used in a secondary battery in the art.

The current collector for the positive electrode may have a thickness of about 3 μm to about 100 μm. A material for the current collector is not limited as long as the material has high conductivity while not causing any chemical change in a corresponding battery. The material for the current collector may be, for example, stainless steel, aluminum, nickel, titanium, calcinated carbon; aluminum or stainless steel which is surface-treated with carbon, nickel, titanium, silver, or the like. In an embodiment, fine uneven structures may be formed on the surface of the current collector to increase the bonding force of the positive active material, and the current collector may be used in various forms such as a film, a sheet, a foil, a net, a porous body, a foam, or a nonwoven fabric.

The prepared positive active material composition may be coated and dried directly on the current collector for a positive electrode to produce a positive electrode plate. In one or more embodiments, the positive active material composition is cast on a separate support, and then a film exfoliated from the support is laminated on the current collector for a positive electrode to prepare the positive electrode plate.

The positive electrode and the negative electrode may be separated by a separator, and the separator may be any material that is used for a lithium battery in the art. A material for forming the separator may be any material that has a low resistance to ion migration of an electrolyte and has excellent electrolytic solution-retaining capability. As the separator, an insulating thin film having high ion permeability and mechanical strength is used.

The pore diameter of the separator may be in the range of about 0.01 μm to about 10 μm, and the thickness thereof may be in the range of about 5 μm to about 20 μm. Examples of the separator are a sheet or non-woven fabric including an olefin-based polymer such as polypropylene; or glass fiber, polyethylene or the like. When a solid polymer electrolyte is used as the electrolyte, the solid polymer electrolyte may be used as a separator.

In an embodiment, the separator may be a single film formed of the olefin-based polymer, such as poly ethylene, polypropylene, or polyvinylidene fluoride, or a multilayer film of these. In an embodiment, the separator may be a mixed multilayer film, such as a two-layered separator having the structure of polyethylene/polypropylene, a three-layered separator having the structure of polyethylene/polypropylene/polyethylene, or a three-layered separator having the structure of polypropylene/polyethylene/polypropylene.

The electrolyte may be selected from the electrolytes described above.

Lithium batteries are classified into a lithium ion battery, a lithium ion polymer battery, and a lithium polymer battery, depending on the type of the separator and the electrolyte used. Lithium batteries are classified into a cylindrical shape, a square shape, a coin shape, a pouch shape, or the like, depending on the shape. Lithium batteries are classified into a bulk type battery and a thin type battery, depending on the size. Lithium primary batteries and lithium secondary batteries may be used as the lithium battery herein.

The lithium battery may be a lithium ion battery. The lithium battery may be a lithium ion battery having a charging voltage of 4.3 V or more.

The lithium battery may be a lithium metal battery including a lithium negative electrode, a positive electrode, and the above-described electrolyte therebetween.

The lithium battery is suitable for applications requiring a high capacity, high output, and high-temperature driving such as an electric vehicle, in addition to, mobile phones and portable computers of the related art. In addition, the lithium battery is combined with existing internal combustion engines, fuel cells, and supercapacitors for use in a hybrid vehicle or the like. Furthermore, the lithium battery may be used for all other applications requiring high output, high voltage, and high-temperature driving.

Methods for manufacturing these batteries are well known in the art, and therefore, detailed description thereof will be omitted.

FIG. 1 shows a schematic structure of a lithium metal battery 11 including an electrolyte according to an embodiment.

As shown in FIG. 1, the lithium metal battery 11 includes a positive electrode 13, a lithium negative electrode 12, and a separator 14. The positive electrode 13, the lithium negative electrode 12, and the separator 14 are wound or folded and housed in a battery case 15. Then, an electrolyte according to an embodiment is injected into the battery case 15 and sealed with a cap assembly (not shown) to complete the manufacture of the lithium metal battery 11. The battery case 15 may have a cylindrical shape, a rectangular shape, a thin film shape, or the like. For example, the lithium metal battery may be a large-film battery. The lithium metal battery may be a lithium-ion battery.

The lithium metal battery, due to its excellence in capacity and lifespan, may be used for a battery cell used as a power source for a small device. In addition, the lithium metal battery may be used for a medium- or large-sized battery pack or a battery module including a plurality of battery cells used as power source of medium- or large-sized devices.

Examples of the medium and large-sized devices include an electric vehicle (EV), a hybrid electric vehicle (HEV), a plug-in hybrid electric vehicle (PHEV), and the like.

The lithium metal battery shows excellent stability at a high voltage of 4.35 V or higher, for example, about 4.4 V to about 4.5 V (vs. Li/Li$^+$).

In an embodiment, the lithium battery may be a lithium air battery including an electrolyte according to an embodiment.

Figure 9:
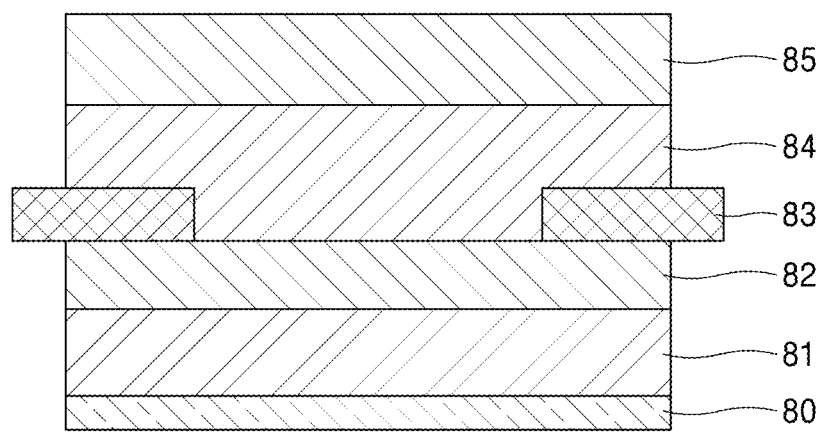
FIG. 9 is a schematic view of a lithium air battery according to an embodiment.

FIG. 9 shows a schematic view of a lithium air battery according to an embodiment.

Referring to FIG. 9, the lithium air battery includes a positive electrode 84 using oxygen as an active material placed on the gas diffusion layer 85 and a lithium metal negative electrode 81 with a copper thin film 80, which is a negative electrode current collector, placed thereon. An electrolyte 82 according to an embodiment may be located on the lithium metal negative electrode 81. A mask layer 83 is located between the electrolyte 82 and the positive electrode 84. Herein, the mask layer 83 may act as an interlayer or a film for the protection of a lithium negative electrode, and may include, for example, a polyoxyethylene methacrylate (POEM) polymer substituted with a fluorine-based or carbonate-based functional group.

An electrolyte according to an embodiment is also applicable to a three-dimensional (3D) lithium air battery.

Figure 2:
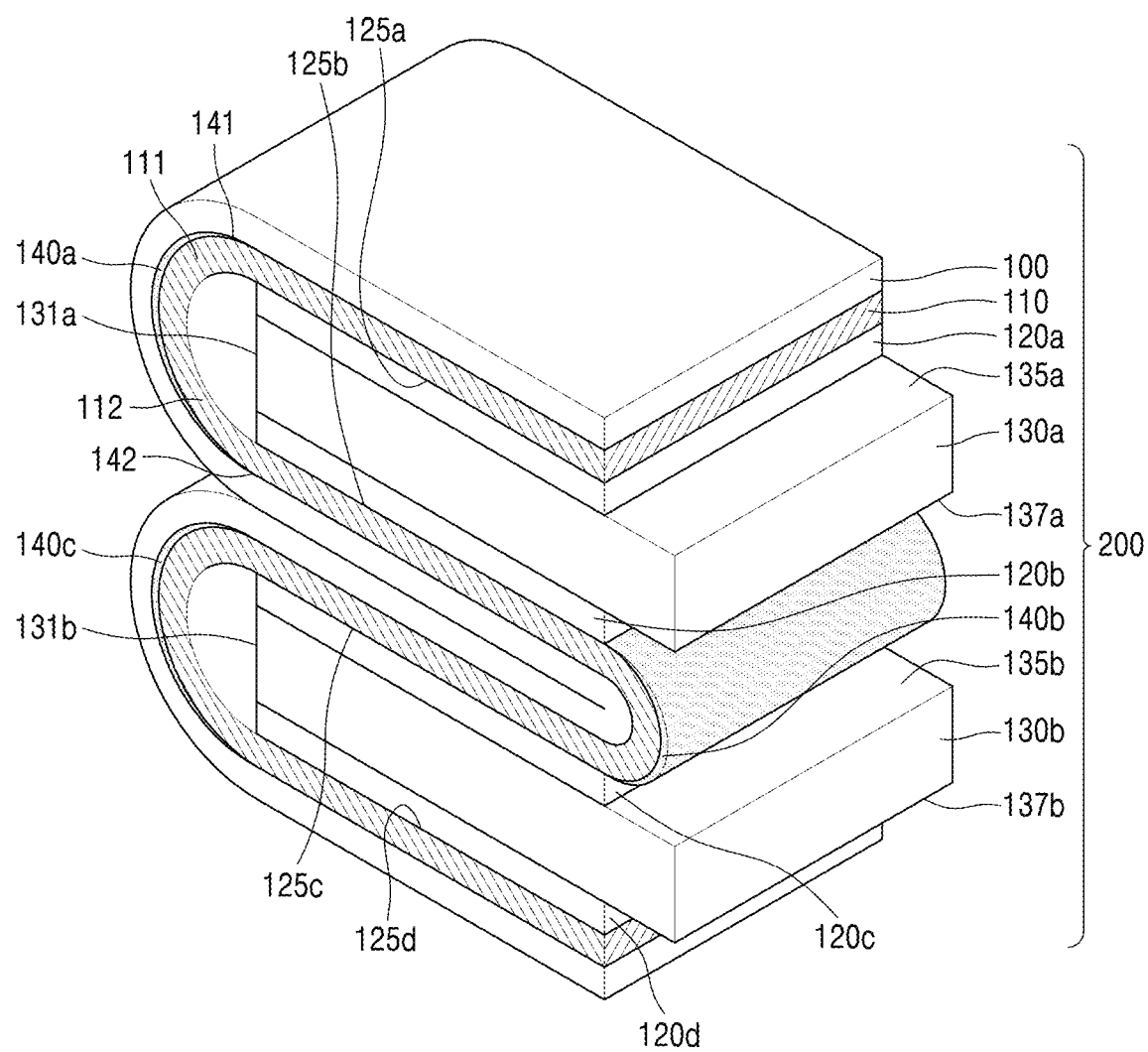
FIG. 2 is a schematic view of a three-dimensional (3D) lithium air battery according to an embodiment.
Figure 3:
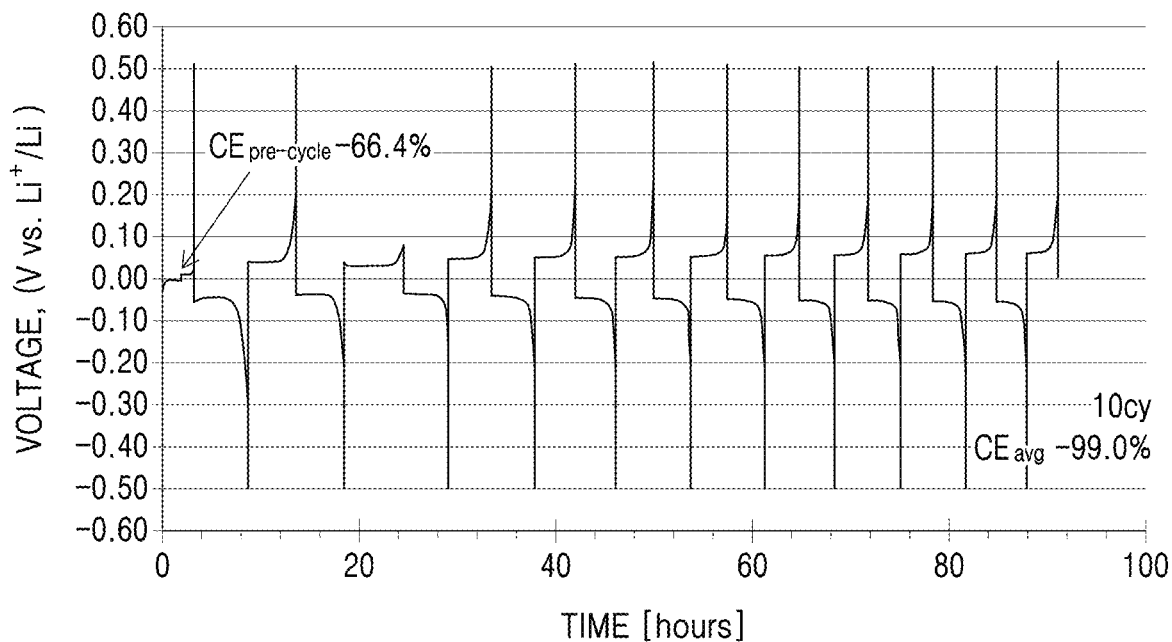
FIG. 3 is a graph of electrode potential (Volts vs. Li/Li+, V) versus time (hours) showing lifespan characteristics of a lithium metal battery prepared according to Example 1.
Figure 4:
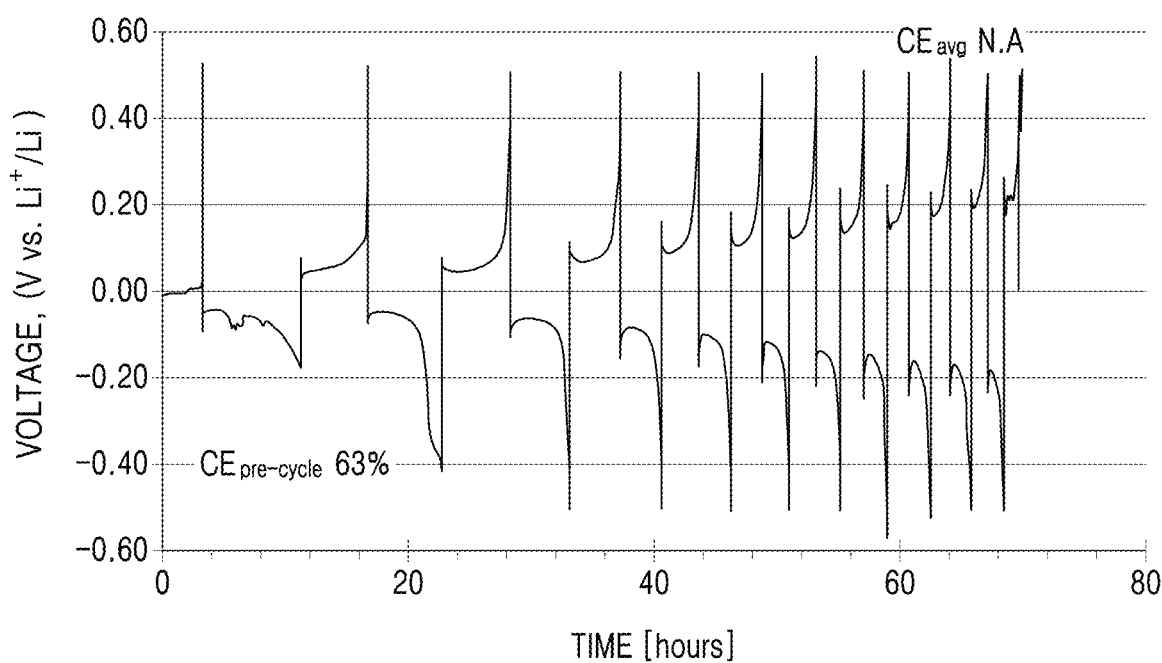
FIG. 4 is a graph of electrode potential (V vs. Li/Li+) versus time (hours) and shows lifespan characteristics of a lithium metal battery prepared according to Comparative Example 1.
Figure 5:
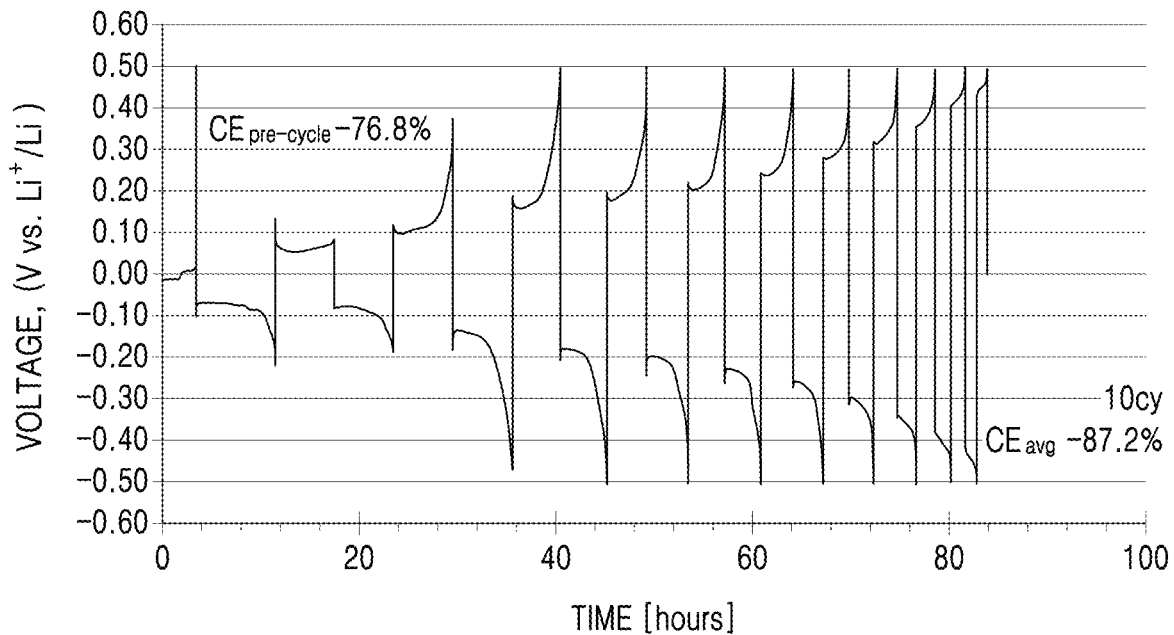
FIG. 5 is a graph of electrode potential (V vs. Li/Li+) versus time (hours) and shows lifespan characteristics of a lithium metal battery prepared according to Comparative Example 2.
Figure 6:
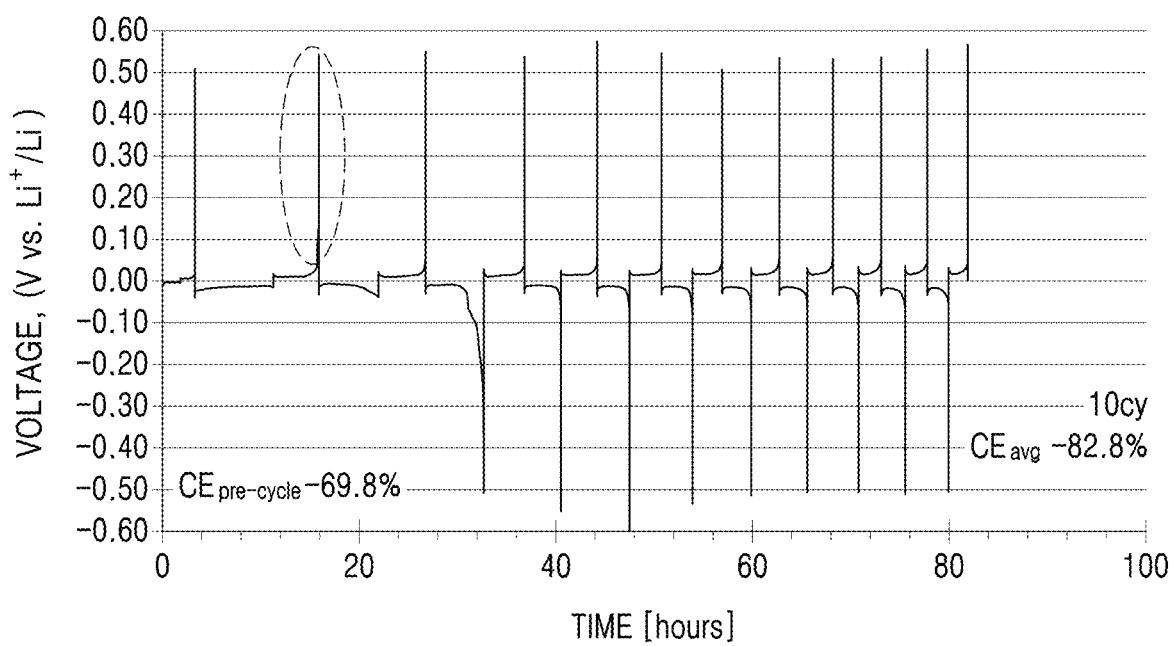
FIG. 6 is a graph of electrode potential (V vs. Li/Li+) versus time (hours) and shows lifespan characteristics of a lithium metal battery prepared according to Comparative Example 4.

Referring to FIG. 2, the 3D lithium air battery 200 includes a plurality of gas diffusion layers 130a and 130b which are spaced apart from each other in their thickness directions, a plurality of first positive electrodes 120a and 120c respectively on surfaces 135a and 135b of the gas diffusion layers 130a and 130b and a plurality of second positive electrodes 120b and 120d respectively on other surfaces 137a and 137b of the gas diffusion layers 130a and 130b, an ion conductive film 110 repeatedly bent at the angle of 180 degrees such that the ion conductive film 110 contacts each of surfaces 125a, 125b, 125c, and 125d of the first positive electrodes 120a and 120c and the second positive electrodes 120b and 120d, and a negative electrode 100 conforming to the ion conductive film 110 while in contact with the ion conductive film 110 and folded at the angle of 180 degrees between the gas diffusion layers 130a and 130b which are adjacent to each other.

The ion conductive film 110 may include an electrolyte according to an embodiment.

In the 3D lithium air battery 200, the first positive electrodes 120a and 120c and the second positive electrodes 120b and 120d are not located on side surfaces 131a and 131b of the gas diffusion layers 130a and 130b. Accordingly, even when the ion conductive film 110 cracks, the negative electrode 100 and the first positive electrodes 120a and 120b may not be short-circuited.

The 3D lithium air battery 200 may include a plurality of interlayers 140a, 140b, and 140c containing a reinforcing agent located in contact with bent portions 111 and 112 of the ion conductive film 110. Due to the inclusion of the interlayers 140a, 140b and 140c in the 3D metal-air battery 200, cracking of the ion conductive film 110 and short-circuit of the negative electrode 100 and the first positive electrode 120a and the second positive electrode 120b may be prevented.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those of ordinary skill in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions.

The definitions of substituents and groups used in the formulas described herein are as follows.

The term "hydrocarbon" as used herein refers to any chemical group comprising hydrogen and carbon. The hydrocarbon may be substituted or unsubstituted.

The term "alkyl" used herein refers to fully saturated branched or unbranched (or linear) hydrocarbon group. Non-limiting examples of the alkyl group include methyl, ethyl, n-propyl, isopropyl, n-butyl, isobutyl, sec-butyl, n-pentyl, isopentyl, neopentyl, n-hexyl, 3-methylhexyl, 2,2-dimethylpentyl, 2,3-dimethylpentyl, n-heptyl, and the like.

At least one hydrogen atom of the alkyl group may be substituted (i.e., replaced) with a halogen atom, a C1-C20 alkyl group substituted with a halogen atom (for example: $CF_3$, $CHF_2$, $CH_2F$, $CCl_3$, etc.), a C1-C20 alkoxy group, a C2-C20 alkoxyalkyl group, a hydroxyl group, a nitro group, a cyano group, an amino group, an amidino group, a hydrazine group, a hydrazone group, a carboxyl group or a salt thereof, a sulfonyl group, a sulfamoyl group, a sulfonic acid group or a salt thereof, a phosphoric acid group or a salt thereof, a C1-C20 alkyl group, a C2-C20 alkenyl group, a C2-C20 alkynyl group, a C1-C20 heteroalkyl group, a C6-C20 aryl group, a C7-C20 arylalkyl group, a C6-C20 heteroaryl group, a C7-C20 heteroarylalkyl group, a C6-C20 heteroaryloxy group, a C6-C20 heteroaryloxyalkyl group, or a C6-C20 heteroarylalkyl group.

As used herein, with regard to the term "substituted or unsubstituted" group, "substituted" means at least one hydrogen atom of a group is substituted with one or more of the substituent groups as described above in connection with the alkyl group.

The term "halogen atom" used herein includes fluorine, bromine, chlorine, iodine, and the like.

The term "C1-C20 alkyl group substituted by a halogen atom" as used herein refers to a C1-C20 alkyl group substituted with at least one halo group, and includes a a monohaloalkyl, and a polyhaloalkyl such as a dihaloalkyl, or a perhaloalkyl.

The term "monohaloalkyl" as used herein refers to an alkyl group that is substituted with one iodine atom, one bromine atom, one chlorine atom, or one fluorine atom, and a dihaloalkyl and a polyhaloalkyl each refer to an alkyl group substituted with two or more identical or different halogen atoms.

The term "alkoxy" used herein is a group represented by the formula alkyl-O—, wherein the alkyl is the same as described above for the alkyl group. Non-limiting examples of the alkoxy group include methoxy, ethoxy, propoxy, 2-propoxy, butoxy, tert-butoxy, pentyloxy, hexyloxy, and the like. At least one hydrogen atom in the alkoxy group may be substituted with one or more of the same substituent groups as described above in connection with the alkyl group.

The term "alkoxyalkyl" used herein refers to the case where the alkyl group is substituted with the alkoxy group described above. At least one hydrogen atom in the alkoxyalkyl group may be substituted with one or more of the same substituent groups as described above in connection with the alkyl group. As such, the term "alkoxyalkylene" includes substituted alkoxyalkylene moieties.

The term "alkenyl" as used herein refers to branched or unbranched hydrocarbon groups having at least one carbon-carbon double bond. Non-limiting examples of the alkenyl group include vinyl, allyl, butenyl, isopropenyl, isobutenyl, and the like. At least one of the hydrogen atoms of the alkenyl group may be substituted with one or more of the same substituent groups as described above in connection with the alkyl group.

The term "alkynyl" as used herein refers to branched or unbranched hydrocarbon groups having at least one carbon-carbon triple bond. Non-limiting examples of the alkynyl group include ethynyl, butynyl, isobutynyl, isopropynyl, and the like. At least one hydrogen atom in the alkynyl group may be substituted with one or more of the same substituent groups as described above in connection with the alkyl group.

The term "aryl" as used herein refers a monocyclic or polycyclic aromatic group containing only carbon in the aromatic rings. For example, aryl groups contain 1 to 3 separate, fused, or pendant aromatic rings and from 6 to about 24 ring atoms, without heteroatoms as ring members. Aryl groups further include groups in which an aromatic ring is fused to at least one carbocyclic group. Non-limiting examples of the aryl groups include phenyl, naphthyl, tetrahydronaphthyl, and the like. At least one hydrogen atom in the aryl group may be substituted with one or more of the same substituent groups as described above in connection with the alkyl group.

The term "arylalkyl" as used herein refers to an alkyl group substituted with an aryl group. Examples of arylalkyl groups include benzyl or phenyl-$CH_2CH_2$—.

The term "aryloxy" used herein is represented by —O-aryl, and examples of the aryloxy group include phenoxy and the like. At least one hydrogen atom in the aryloxy group may be substituted with the same substituent as described above in connection with the alkyl group.

The term "heteroaryl" as used herein refers to a monocyclic or polycyclic (e.g., bicyclic) aromatic group having at least one ring atom replaced by at least one heteroatom selected from N, O, P, and S, and with the remaining aromatic ring atoms being carbon. The heteroaryl group may contain, for example, 1 to 5 heteroatoms, and 5 to 25 aromatic ring atoms in total. The heteroatoms S or N may be oxidized to have various oxidation states. As used herein, the term aromatic ring encompasses both aryl and heteroaryl groups.

Examples of monocyclic heteroaryl groups include thienyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazole-2-yl, oxazole-4-yl, oxazole-5-yl, isooxazole-3-yl, isooxazole-4-yl, isooxazole-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, pyrazine-2-yl, pyrazine-4-yl, pyrazine-5-yl, pyrimidine-2-yl, pyrimidine-4-yl, pyrimidine-5-yl, and the like.

The heteroaryl group further includes a group in which a heteroatom-containing aromatic ring is fused to one or more aryl, cycloaliphatic, or heterocyclic groups.

Examples of bicyclic heteroaryl groups include indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxazepinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, and the like.

At least one hydrogen atom in the "heteroaryl" group may be substituted with one or more of the same substituent groups as described above in connection with the alkyl group.

The term "heteroarylalkyl" as used herein refers to an alkyl group substituted with a heteroaryl group.

The term "heteroaryloxy" as used herein refers to a group of the formula —O-heteroaryl. At least one hydrogen atom in the heteroaryloxy group may be substituted with one or more of the same substituent groups as described above in connection with the alkyl group.

The term "heteroaryloxyalkyl" as used herein refers to an alkyl group substituted with a heteroaryloxy group. At least one hydrogen atom in the heteroaryloxyalkyl group may be substituted with one or more of the same substituent groups as described above in connection with the alkyl group.

The term "carbocyclic" as used herein refers to a non-aromatic ring group containing only carbon atoms as ring members, and includes saturated and partially unsaturated non-aromatic monocyclic, bicyclic, and tricyclic hydrocarbon groups. Examples of the monocyclic hydrocarbon groups include cyclopentyl, cyclopentenyl, cyclohexyl, cyclohexenyl, and the like. Examples of the bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl, and the like. Examples of the tricyclic hydrocarbon groups include adamantyl and the like. At least one hydrogen atom in the carbocyclic group may be substituted with one or more of the same substituent groups as described above in connection with the alkyl group.

The term "carbocyclicalkyl" as used herein refers to an alkyl group substituted with a carbocyclic group. At least one hydrogen atom in the carbocyclicalkyl group may be substituted with one or more of the same substituent groups as described above in connection with the alkyl group.

The term "heterocyclic" as used herein refers to a non-aromatic ring group containing 5 to 10 ring atoms and containing 1 to 3 heteroatoms such as nitrogen, sulfur, phosphorus, oxygen, and the like, and examples thereof include pyridyl and the like. At least one hydrogen atom in such a heterocyclic group may be substituted with one or more of the same substituent groups as described above in connection with the alkyl group.

The term "heterocyclicalkyl" as used herein refers to an alkyl group substituted with a heterocyclic group. At least one hydrogen atom in the heterocyclicalkyl group may be substituted with one or more of the same substituent groups as described above in connection with the alkyl group.

The term "heterocyclicoxy" as used herein refers to a group of the formula —O-heterocyclic, and at least one hydrogen atom in the heterocyclicoxy group may be substituted with one or more of the same substituent groups as described above in connection with the alkyl group.

The term "sulfonyl" as used herein refers to a group of the formula (—S(=O)$_2$—R"), wherein R" is hydrogen, halogen, alkyl, aryl, heteroaryl, arylalkylene, heteroarylalkylene, alkoxy, aryloxy, cycloalkyl, or heterocyclic group. At least one hydrogen atom in the sulfonyl group may be substituted with one or more of the same substituent groups as described above in connection with the alkyl group.

The term "sulfamoyl" as used herein includes groups of the formulae H$_2$NS(O$_2$)—, alkyl-NHS(O$_2$)—, (alkyl)$_2$NS(O$_2$)—, aryl-NHS(O$_2$)—, alkyl-(aryl)-NS(O$_2$)—, (aryl)$_2$NS(O)$_2$, heteroaryl-NHS(O$_2$)—, (arylalkyl)-NHS(O$_2$)—, or (heteroarylalkyl)-NHS(O$_2$)—. At least one hydrogen atom in the sulfamoyl group may be substituted with one or more of the same substituent groups as described above in connection with the alkyl group.

The term "thio" as used herein refers to a group of the formula —SR, wherein R is halogen, hydrogen, alkyl, heteroalkyl, carbocyclic, heterocyclic, aryl, or heteroaryl. At least one hydrogen of the thio group may be substituted with one or more of the same substituent groups as described above in connection with the alkyl group.

The term "sulfonic acid" group as used herein refers to a group of the formula —SO$_3$H$_2$, and further includes a sulfonic mono- or dibasic salt (—SO$_3$MH or —SO$_3$M$_2$ wherein M is an organic or inorganic cation).

The term "phosphoric acid" group as used herein refers to a group of the formula —PO$_3$H$_2$, and further includes a phosphoric acid mono- or dibasic salt (—PO$_3$MH or —PO$_3$M$_2$ wherein M is an organic or inorganic cation).

The term "carbamoyl" as used herein refers to a group of the formula —C(O)NH$_2$.

The term "carbonyl" as used herein refers to a group of the formula —C(=O)R, wherein R is halogen, hydrogen, alkyl, aryl, heteroalkyl, heteroaryl, alkoxy, or aryloxy.

The term "carboxylic acid" group as used herein refers to a group of the formula —C(=O)OH, and further includes a carboxylic acid salt of the formula —C(=O)OM, wherein M is an organic or inorganic cation.

The term "cyano" as used herein refers to a group of the formula —CN.

The term "isothiocyanate" as used herein refers to a group of the formula —NCS.

The term "thiocyanate" as used herein refers to a group of the formula —SCN.

The term "cyanato" as used herein refers to a group of the formula —OCN.

The term "isocyanato" as used herein refers to a group of the formula —NCO.

The term "amino" as used herein refers to a nitrogen-containing group where the nitrogen atom is covalently bonded to at least one carbon atom or heteroatom. For example, the amino group can be a group of the formula —NR'R" wherein R' and R" are each independently selected from hydrogen, substituted or unsubstituted alkyl, substituted or unsubstituted heteroalkyl, carbonyl, substituted or unsubstituted carbocyclic, substituted or unsubstituted heterocyclic, substituted or unsubstituted aryl, or substituted or unsubstituted heteroaryl. The point of attachment of the amino group is on the nitrogen atom and not the groups R' or R". The amino group includes, for example, —NH$_2$ and substituted moieties thereof. The term amino group further includes an "alkyl amino" group in which a nitrogen atom is bonded to at least one additional alkyl group, and an "aryl amino" group and a "diaryl amino" group wherein the nitrogen atom is bonded to one or two aryl groups, respectively, wherein the aryl groups are each independently selected from the aryl groups as described herein. The amino group further includes a group wherein the R' and R" moieties are connected to form a ring structure with the nitrogen atom, such as in morpholine, which is a group of the formula —N(CH$_2$CH$_2$)$_2$O.

As used herein, the terms "alkylene", "arylene", and "heteroarylene" represent a divalent group obtained from an alkyl, aryl, and heteroaryl group, respectively. The arylene and heteroarylene groups also include trivalent and tetravalent groups. As used herein, the terms "alkenylene" and "alkynylene" represent a divalent group obtained from an alkenyl and alkynyl group, respectively.

The expression * as used herein indicates a binding site to a neighboring atom, unless otherwise stated.

Embodiments of the present disclosure will be described in more detail with reference to the following examples and comparative examples. These examples are provided herein for illustrative purpose only, and do not limit the scope of the present disclosure.

EXAMPLES

Example 1

(1) Synthesis of Metallic Salt Having Heterocyclic Aromatic Structure

Lithiated 5-methyl-3-(trifluoromethyl)-1,2,4-triazolate was prepared as a metallic salt as shown in Reaction Scheme 1 and according to the following procedure.

Reaction Scheme 1

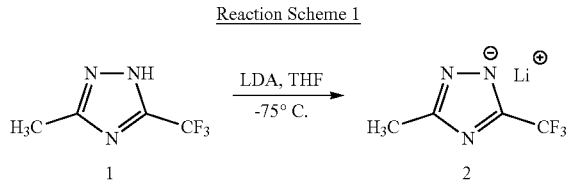

First, under an argon atmosphere, a diethyl ether (100 mL) solution of diisopropylamine (7.58 mL, 54.155 mmol) was cooled to a temperature of −30° C. to −40° C., and then, lithium diisopropylamide (LDA) (19.8 mL, 49.642 mmol, 2.5 M) was dropwise added thereto. The resulting reaction mixture was cooled to −75° C., and a diethyl ether (50 mL)/THF (20 mL) solution of Compound 1 (7 g, 45.129 mmol) was added dropwise thereto for 1 hour. The result was stirred and the temperature thereof was increased to room temperature. The resulting mixture was concentrated under reduced pressure to remove the solvent therefrom, followed by addition of a mixed solvent of diethyl ether/hexane (1:9 by volume) and then filtration of a solid therefrom. Toluene was added to the obtained solid, followed by sonication and filtration to obtain metallic salt (6.8 g, 94%) of Compound 2 as a pale brown solid.

(2) Manufacture of Liquid Electrolyte and Lithium Metal Battery

The synthesized metallic salt was mixed with ethylene glycol dimethyl ether (1,2-dimethoxyethane) (DME) at a concentration of 1M to prepare a liquid electrolyte.

A polyethylene/polypropylene separator was placed between a lithium metal electrode (thickness: about 20 μm) and a copper metal electrode (thickness: about 15 μm), and the liquid electrolyte was added thereto to manufacture a LiCu 2 electrodes cell.

Example 2

A starting material, benzotriazole, was dissolved in the solvent THF, and lithium bis(trimethylsilyl)amide (LHMDS) was slowly added at 1.2 eq. dropwise to the reaction mixture in an ice bath (−5° C. to 0° C.), followed by stirring for 12 hours to remove the solvent therefrom. The formed solid was washed three times with 20 mL of hexane each time, and the washed solid was dried under vacuum at 60° C. for 24 hours to obtain lithiated benzotriazolate having the following formula as a metallic salt in powder form.

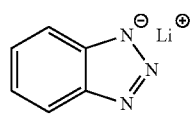

A liquid electrolyte and a lithium metal battery were produced in the same manner as in Example 1, except that the lithiated benzotriazolate as the metallic salt was used.

Example 3

Lithiated 4,5,6,7-tetrafluoro-benzotriazolate was prepared as a metallic salt as shown in Reaction Scheme 2 and according to the following procedure.

Reaction Scheme 2

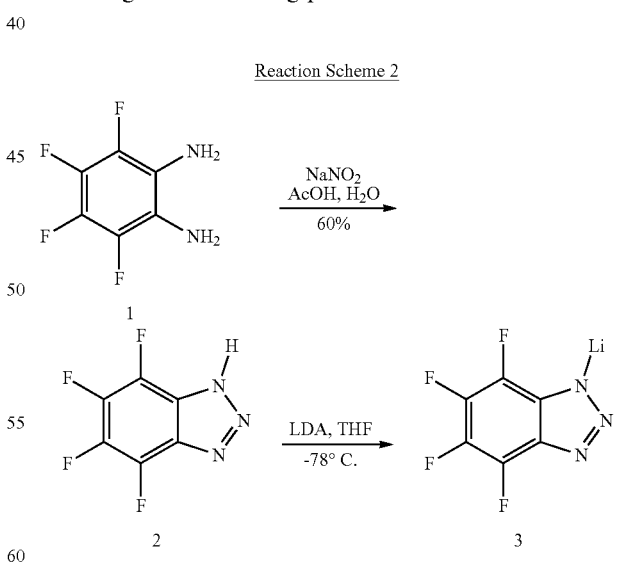

12 mL of acetic acid was added to a suspension where 18 g of 3,4,5,6-tetrafluoro-1,2-phenylenediamine of Compound 1 as a starting material was dispersed in water, and then, an aqueous solution of 8.5 g of sodium nitrite was added thereto. The reaction mixture was heated to 85° C. while stirring, and under ice bath, stirred and filtered for 30 minutes, and washed with water and hexane, followed by drying. The dried solid was purified by column to obtain Compound 2 (11.2 g, 76%) as a white yellow solid.

Under Ar atmosphere, lithium diisopropylamide (LDA) (20 mL, 2.5 M) was added dropwise to a diethyl ether solution (100 mL) of diisopropylamine (8.5 mL). 50 ml of THF solution of Compound 2 (6.5 g) was added dropwise for 1 hour. After stirring, the solvent was removed therefrom, and toluene was added to the obtained solid to perform sonication for 30 minutes. Then, filtration was performed to obtain a metallic salt of Compound 3 (7.2 g, 90%) as a pale brown solid.

A liquid electrolyte and a lithium metal battery were produced in the same manner as in Example 1 except that lithiated 4,5,6,7-tetrafluoro-benzotriazolate was used.

Example 4

Lithiated fluoro-benzotriazolate was prepared as a metallic salt as shown in Reaction Scheme 3 and according to the following procedure.

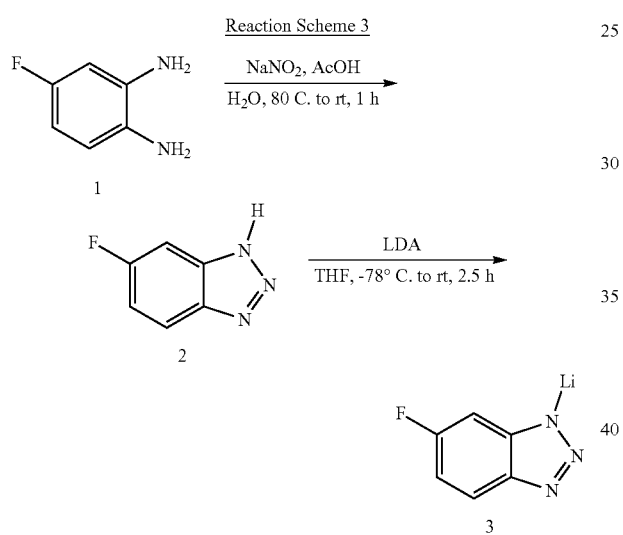

11 mL of acetic acid were added to a suspension where 13.2 g of 1-amino-4-fluorobenzene of Compound 1 as a starting material was dispersed in water. An aqueous solution of sodium nitrite (7 g) was added thereto and reacted. The reaction mixture was heated to 80° C. while stirring, and under ice bath, stirred and filtered for 1 hour, and washed with water and hexane, followed by drying. The dried solid was purified by column to obtain Compound 2 (12.5 g, 83%) as a dark brown solid.

Under Ar atmosphere, lithium diisopropylamide (LDA) (20 mL, 2.5 M) was added dropwise to a diethyl ether solution (100 mL) of diisopropylamine (7.6 mL). 50 ml of THF solution of Compound 2 (7 g) was added dropwise for 1 hour. After stirring, the solvent was removed therefrom, toluene was added to the obtained solid to perform sonication for 1.5 hour. Then, filtration was performed to obtain a metallic salt of Compound 3 (6.8 g, 94%) as a pale brown solid.

A liquid electrolyte and a lithium metal battery were produced in the same manner as in Example 1 except that the Lithiated fluoro-benzotriazolate was used.

Comparative Example 1

Lithiated 3,5-bis(trifluoromethyl)-1,2,4-triazolate having the following formula was prepared as a metallic salt by a method similar to that of Example 1. Here, 3,5-bis(trifluoromethyl)-1,2,4-triazole was used instead of Compound 1 used in Example 1.

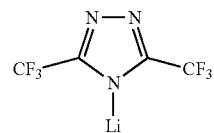

A liquid electrolyte and a lithium metal battery were produced in the same manner as in Example 1 except that lithiated 3,5-bis(trifluoromethyl)-1,2,4-triazolate was used.

Comparative Example 2

The starting material, 5-(trifluoromethyl)-tetrazole, was dissolved in the solvent THF, and then, lithium bis(trimethylsilyl)amide (LHMDS) was slowly added at 1.2 eq. dropwise to the reaction mixture in an ice bath (−5° C. to 0° C.), followed by stirring for 12 hours to remove the solvent therefrom. The formed solid was washed three times with 20 ml of hexane each time, and the washed solid was dried under vacuum at 60° C. for 24 hours to obtain lithiated 5-(trifluoromethyl)-tetrazolate having the following formula as a metallic salt in powder form.

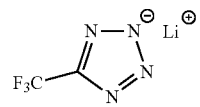

A liquid electrolyte and a lithium metal battery were produced in the same manner as in Example 1 except that lithiated 5-(trifluoromethyl)-tetrazolate was used.

Comparative Example 3

The starting material, 1,2,4-triazole, was dissolved in the solvent THF, and lithium bis(trimethylsilyl)amide (LHMDS) was slowly added at 1.2 eq. dropwise to the reaction mixture in an ice bath (−5° C. to 0° C.), followed by stirring for 12 hours to remove the solvent therefrom. The formed solid was washed three times with 20 ml of hexane each time, and the washed solid was dried under vacuum at the temperature of 60° C. for 24 hours to obtain lithiated 1,2,4-triazolate having the following formula as a metallic salt in powder form.

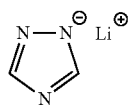

A liquid electrolyte and a lithium metal battery were produced in the same manner as in Example 1 except that lithiated 1,2,4-triazolate was used.

Comparative Example 4

A liquid electrolyte and a lithium metal battery were prepared in the same manner as in Example 1, except that lithium bis(trifluoromethanesulfonyl)imide (LiTFSI) was used as a metallic salt.

Comparative Example 5

A liquid electrolyte and a lithium metal battery were prepared in the same manner as in Example 1, except that lithium bis(trimethylsilyl)amide (LHMDS) was used as a metallic salt.

Evaluation Example 1: Characterization of Metallic Salt and Evaluation of Negative Electrode Efficiency The purity, lithium substitution degree, and lithium-negative-electrode efficiency of the metallic salts of Examples 1-4 and Comparative Examples 1-5 were measured, and the results are shown in Table 1 below.

The purity of the metallic salt may be measured by using high-performance liquid chromatography (HPLC, HPLC 2695, waters 2695), and the lithium substitution degree thereof may be measured by using ion chromatography (IC, ICS5000).

The efficiency of the lithium negative electrode was obtained through the calculation of mean lithium metal coulombic efficiency (calculation $CE_{avg}$) as follows.

The mean lithium metal coulombic efficiency (calculation $CE_{avg}$) was measured using the Li—Cu two electrode cell. Li was completely stripped from a pretreated Cu support up to 0.5 V with a capacity of 1 mAh/cm$^2$ and a current density of 0.1 mA/cm$^2$. Once a Li reservoir ($Q_T$=4.0 mAh/cm$^2$) was formed on the Cu support, charging and discharging cycles were performed during 10 cycles at 1.0 mA/cm$^2$, and the final stripping ($Q_s$) was performed at 1.0 mA/cm$^2$, up to 0.5 V, followed by the termination of this experiment. The mean coulombic efficiency was calculated by Equation 1.

$$CE_{avg} = \frac{nQ_C + Q_S}{nQ_C + Q_T} \quad \text{Equation 1}$$

wherein $Q_c$ is a fixed amount of Li stripped, $Q_s$ is an exhaustive stripping of Li, $Q_T$ is excess Li deposited onto Cu, and n is the number of cycles.

The mean coulombic efficiency calculation is described in *Advanced Energy Material*, 2017, 1702097, which is incorporated by reference herein.

TABLE 1

| | Structure of metallic salt | HPLC | IC | Efficiency of lithium negative electrode |
|---|---|---|---|---|
| Example 1 | [structure] | 98% | 97% | 99% |
| Example 2 | [structure] | 96% | 98% | 96% |
| Example 3 | [structure] | 98% | 97% | 98% |
| Example 4 | [structure] | 98% | 97% | 93% |
| Comparative Example 1 | [structure] | 97% | 94% | NA |
| Comparative Example 2 | [structure] | 99% | 100% | 87% |
| Comparative Example 3 | [structure] | 95% | 98% | 81% |
| Comparative Example 4 | [structure] | 95% | 97% | 83% |
| Comparative Example 5 | [structure] | 94% | 94% | 59% |

As shown in Table 1, the metallic salts of Examples 1 to 4 have higher efficiency of the lithium negative electrode than the metallic salts of Comparative Examples 1 to 5.

As shown in Example 1, the 1,2,4-triazolate metallic salt in which the electron-donating group and the electron-withdrawing group were simultaneously substituted showed the highest lithium-negative-electrode efficiency.

Evaluation Example 2: Lifespan Evaluation

The lithium metal batteries prepared according to Example 1 and Comparative Examples 1, 2, and 4 were charged and discharged at currents of 0.1 C, 0.2 C, 0.5 C, and 1 C based on a capacity of 0.5 mAh/cm$^2$ per area, and then the charge/discharge lifespan was measured with the current of 0.5 C based on a capacity of 0.5 mAh/cm$^2$ per area, and the results are shown in FIGS. 3 to 6, respectively.

Referring to FIGS. 3 to 6, it can be seen that the lithium metal battery manufactured in Example 1 has improved lifespan characteristics as compared with the lithium metal battery manufactured in Comparative Examples 1, 2, and 4.

Evaluation Example 3: Identification of SEI Layer

Figure 7:
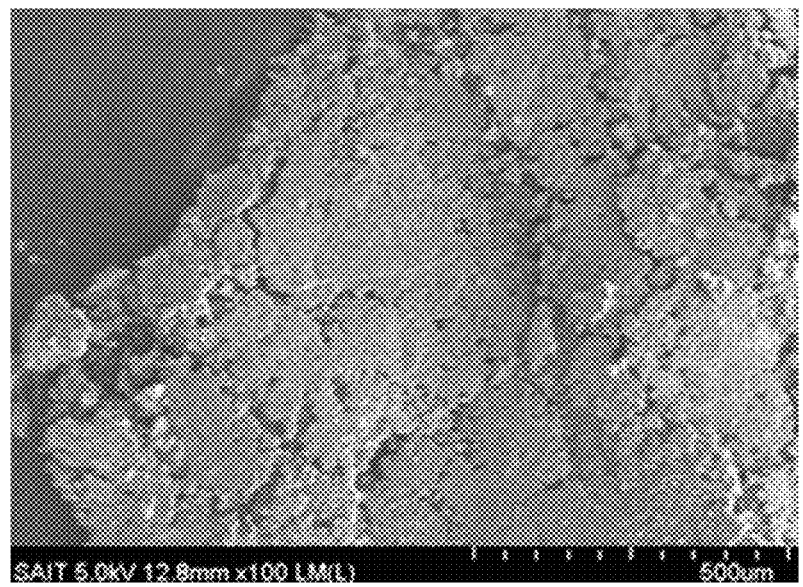
FIG. 7 is an scanning electron microscope (SEM) image of the surface of a lithium negative electrode after the lithium metal battery prepared according to Comparative Example 4 was charged and discharged.
Figure 8:
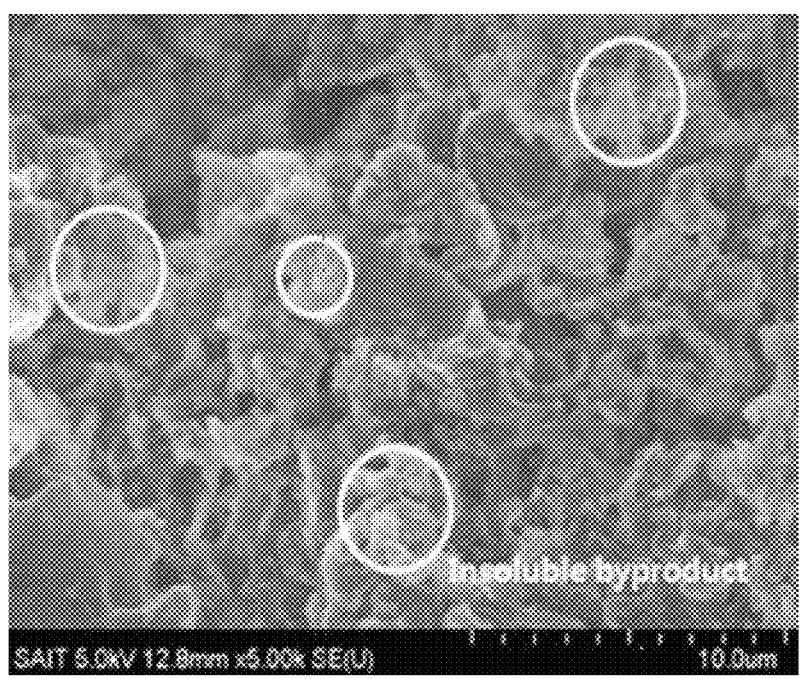
FIG. 8 is an SEM image of the surface of a lithium negative electrode after the lithium metal battery prepared according to Example 1 was charged and discharged.

Scanning electron microscopic (SEM) images of the surface of each of the lithium negative electrodes prepared according to Comparative Example 4 and Example 1 after the charging and discharging of the lithium metal batteries were confirmed, and results thereof are shown in FIGS. 7 and 8, respectively.

As shown in FIG. 7, in the case of Comparative Example 1 using LiTFSI, the layered SEI layer was observed, and as a result of the XPS measurement, the inner portion of the SEI, contacting lithium metal, was identified as a by-product having a composition of $Li_2O$, LiF, and $Li_2S$. Accordingly, it was confirmed that LiTFSI was decomposed during plating/stripping of lithium at a temperature of 60° C., causing the presence of LiF, $Li_2S$, and polysulfides. On the other hand, as shown in FIG. 8, in Example 1, organic byproducts which were not dissolved even by DME washing were confirmed. This may be a dimmer or trimmer structure in which —F is isolated from —$CF_3$ in the metallic salt used in Example 1 and the same structure as the metallic salt is connected. As a result of XPS measurement, LiF was also observed as a decomposition product.

A metallic salt including an anion having the heterocyclic aromatic structure may have electrochemical stability with respect to a negative electrode of an electrochemical device, for example, a lithium metal negative electrode, thereby providing high negative electrode efficiency. As a result, electrochemical devices using the metallic salt may have improved lifespan characteristics.

It should be understood that exemplary embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A metallic salt electrolyte for a battery, comprising:
   at least one anion having a heterocyclic aromatic structure represented by one of Formulae 1 to 3; and
   a metallic cation:

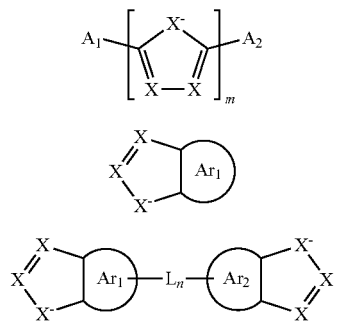

Formula 1

Formula 2

Formula 3 wherein, in Formulae 1 to 3,
each X is independently N, P, or As,
one of $A_1$ and $A_2$ is an electron-donating group, and the other one is an electron-withdrawing group, ring $Ar_1$ and ring $Ar_2$ are each independently an aromatic group that is a substituted or unsubstituted C6 to C24 arylene group or a substituted or unsubstituted C4 to C24 heteroarylene group, wherein the aromatic group comprises a single aromatic ring, two or more aromatic rings which are fused together, or two or more aromatic rings which are connected covalently via a single bond, —O—, —S—, —C(=O)—, —S(=O)$_2$—, —Si($R_a$)($R_b$)— wherein $R_a$ and $R_b$ are each independently a C1 to C10 alkyl group, a substituted or unsubstituted C1 to C10 alkylene group, or —C(=O)—NH—, and wherein $Ar_1$ and $Ar_2$ are each independently unsubstituted or substituted with at least one of an electron-donating group or an electron-withdrawing group, L is a linker group, and is a single bond, —O—, —S—, —C(=O)—, —S(=O)$_2$—, —Si($R_a$)($R_b$)— wherein $R_a$ and $R_b$ are each independently a C1 to C10 alkyl group, —C(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker group is unsubstituted or substituted with at least one of an electron-donating group or an electron-withdrawing group, and wherein the linker group L is non-condensed or condensed with at least one of $Ar_1$ or $Ar_2$, m is an integer from 1 to 5, and n is an integer from 1 to 5.

2. The metallic salt electrolyte of claim 1, wherein the ring $Ar_1$ and the ring $Ar_2$ are each independently selected from the following formulae:

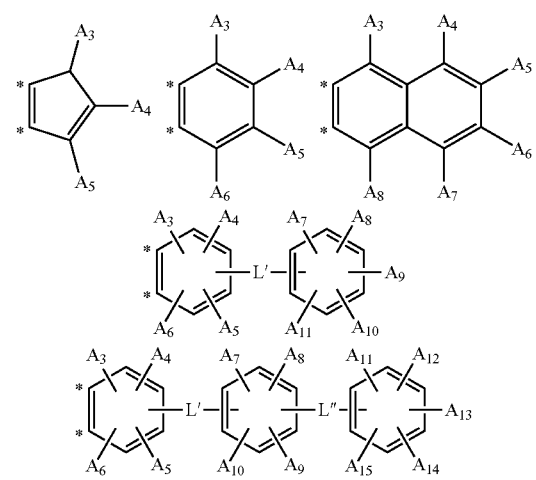

wherein $A_3$ to $A_{15}$ are each independently a hydrogen atom, an electron-donating group, or an electron withdrawing group;

L' and L" are each independently a single bond, —O—, —S—, —C(=O)—, —S(=O)$_2$—, —Si($R_a$)($R_b$)— wherein $R_a$ and $R_b$ are each independently a C1 to C10 alkyl group, —C(=O)—NH—, a C1-C12 alkylene group, a C2-C12 alkenylene group, a C2-C12 alkynylene group, a C6-C12 arylene group, or a C4-C12 heteroarylene group; and

* indicates a binding site to a neighboring atom; and wherein, for Formula 3, at least one of $A_3$ to $A_{15}$ of ring An is linked to at least one of $A_3$ to $A_{15}$ of ring $Ar_2$ by the linker group L.

3. The metallic salt electrolyte of claim 1, wherein the heterocyclic aromatic structure of the anion is represented by one of Formulae 1a, 1b, 1c, 2a, 2b, and 3a:

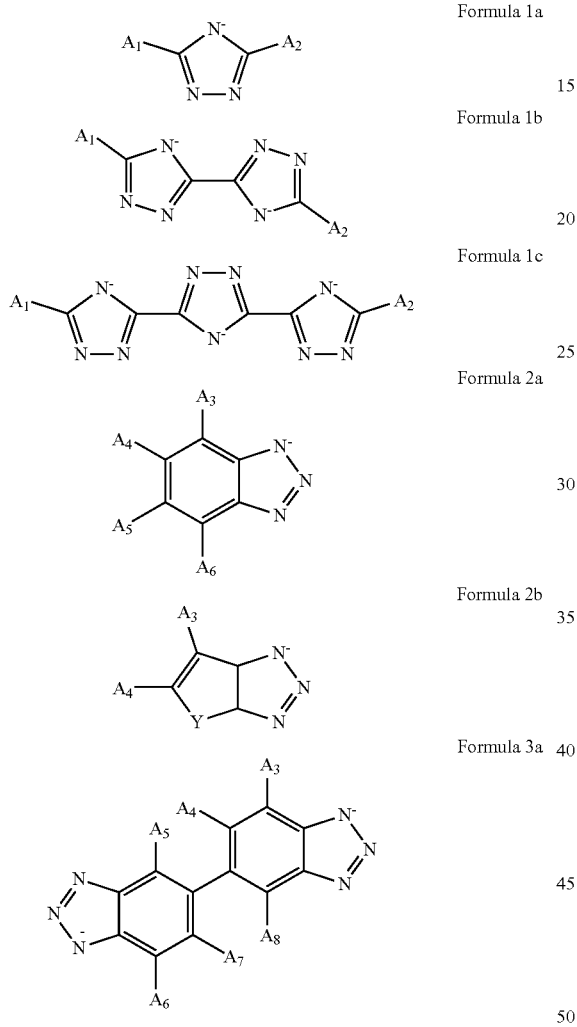

Formula 1a

Formula 1b

Formula 1c

Formula 2a

Formula 2b

Formula 3a wherein, in Formulae 1a to 3a, one of $A_1$ and $A_2$ is an electron-donating group and the other one is an electron-withdrawing group;

$A_3$ to $A_8$ are each independently a hydrogen atom, an electron-donating group, or an electron-withdrawing group; and Y is oxygen, sulfur, or nitrogen.

4. The metallic salt electrolyte of claim 1, wherein the electron-donating group is a substituted or unsubstituted C1-C30 alkyl group, a substituted or unsubstituted C2-C30 alkenyl group, a substituted or unsubstituted C2-C30 alkynyl group, a substituted or unsubstituted C6-C30 aryl group, a substituted or unsubstituted C1-C30 alkoxy group, a substituted or unsubstituted C2-C30 alkoxyalkyl group, a substituted or unsubstituted C6-C30 aryloxy group, a substituted or unsubstituted C7-C30 aryloxyalkyl group, a substituted or unsubstituted C7-C30 arylalkyl group, a substituted or unsubstituted C2-C30 heteroaryl group, a substituted or unsubstituted C2-C30 heteroaryloxy group, a substituted or unsubstituted C3-C30 heteroarylalkyl group, a substituted or unsubstituted C4-C30 carbocyclic group, a substituted or unsubstituted C5-C30 carbocyclicalkyl group, a substituted or unsubstituted C2-C30 heterocyclic group, a substituted or unsubstituted C3-C30 heterocyclicalkyl group, a substituted or unsubstituted amino group, a substituted or unsubstituted carbamoyl group, a hydroxy group, a nitro group, a cyano group, an amino group, an amidino group, a hydrazine group, a hydrazone group, a carboxyl group or salt thereof, a thiol group, a phosphoric acid group or salt thereof, or a combination thereof.

5. The metallic salt electrolyte of claim 1, wherein the electron-donating group is $-C_nH_{2n+1}$, $-OC_nH_{2n+1}$, $-NH_2$, $-NH(C_nH_{2n+1})$, $-N(C_nH_{2n+1})_2$, $-OH$, $-NH(COC_nH_{2n+1})$, $-N(COC_nH_{2n+1})_2$, $-OCOC_nH_{2n+1}$, $-CH_2(C_nH_{2n+1})$, $-CH(C_nH_{2n+1})_2$, $-C(C_nH_{2n+1})_3$, $-SC_nH_{2n+1}$, $-N(CH_2CH_2)_2O$, $-P(O)(OH)_2$, $-P(O)OH$, a phenyl group, a vinyl group, or a combination thereof, and wherein n is an integer from 1 to 10.

6. The metallic salt electrolyte of claim 1, wherein the electron-withdrawing group is a halogen atom, a cyano group, an isothiocyanate group, a thiocyanate group, a cyanato group, an isocyanato group, a fluorine-substituted C1-C30 alkyl group, a fluorine-substituted C2-C30 alkenyl group, a fluorine-substituted C2-C30 alkynyl group, a fluorine-substituted C6-C30 aryl group, a fluorine-substituted C1-C30 alkoxy group, a fluorine-substituted C2-C30 alkoxyalkyl group, a fluorine-substituted C6-C30 aryloxy group, a fluorine-substituted C7-C30 aryloxyalkyl group, a fluorine-substituted C7-C30 arylalkyl group, a fluorine-substituted C2-C30 heteroaryl group, a fluorine-substituted C2-C30 heteroaryloxy group, a fluorine-substituted C3-C30 heteroarylalkyl group, a fluorine-substituted C4-C30 carbocyclic group, a fluorine-substituted C5-C30 carbocyclicalkyl group, a fluorine-substituted C2-C30 heterocyclic group, a fluorine-substituted C3-C30 heterocyclicalkyl group, a fluorine-substituted thio group, a sulfonyl group, a sulfamoyl group, a sulfonic acid group or salt thereof, or a combination thereof.

7. The metallic salt electrolyte of claim 1, wherein the electron-withdrawing group is $-F$, $-Cl$, $-Br$, $-CONH_2$, $-COOC_nH_{2n+1}$, $-COCl$, $-COOH$, $-COC_nH_{2n+1}$, $-CHO$, $-NO_2$, $-SO_3H$, $-C\equiv N$, $-S-C\equiv N$, $N=C=S$, $-N=C=O$, $-C_nF_{2n+1}$, $-OC_nF_{2n+1}$, $-CH_2C_nF_{2n+1}$, $-OC_nF_{2n}H$, $-SC_nF_{2n+1}$, $-SC_nF_{2n}H$, $-OCF=CF_2$, $-SCF=CF_2$, $-SO_2F$, and $-SO_2C_nF_{2n+1}$, or a combination thereof, and wherein n is an integer from 1 to 10.

8. The metallic salt electrolyte of claim 1, wherein at least one hydrogen atom present in Formulae 1 to 3 is substituted with a halogen atom, a C1-C30 alkyl group, a C2-C30 alkenyl group, a C2-C30 alkynyl group, a C1-C30 alkoxy group, a C2-C30 alkoxyalkyl group, a C1-C30 heteroalkyl group, a C6-C30 aryl group, a C7-C30 arylalkyl group, a C2-C30 heteroaryl group, a C3-C30 heteroarylalkyl group, a C2-C30 heteroaryloxy group, a C3-C30 heteroaryloxyalkyl group, a C6-C30 heteroarylalkoxy group, a hydroxy group, a nitro group, a cyano group, an amino group, an amidino group, a hydrazine group, a hydrazone group, a carboxyl group or a salt thereof, a sulfonyl group, a sulfamoyl group, a sulfonic acid group or salt thereof, a phosphoric acid group or salt thereof, or a combination thereof.

9. The metallic salt electrolyte of claim 1, wherein
the metallic cation is an alkali metal cation, an alkaline earth metal cation, a transition metal cation, a post-transition metal cation, a rare earth metal cation, or a combination thereof.

10. The metallic salt electrolyte of claim 1, wherein
the metallic cation is $Li^+$, $Na^+$, $Mg^{2+}$, $Ca^{2+}$, $Sm^{3+}$, $La^{3+}$, $Ho^{3+}$, $Sc^{3+}$, $Al^{3+}$, $Yb^{3+}$, $Lu^{3+}$, $Eu^{3+}$, or a combination thereof.

11. The metallic salt electrolyte of claim 1, wherein
the metallic salt electrolyte is a liquid electrolyte, a gel electrolyte, a solid electrolyte, a polymer ionic liquid electrolyte, or a combination thereof.

12. The metallic salt electrolyte of claim 1, wherein
the metallic salt electrolyte is a liquid electrolyte, and further comprises an organic solvent.

13. The metallic salt electrolyte of claim 12, wherein
an amount of the metallic salt electrolyte is about 0.1 moles per liter to about 7 moles per liter based on an amount of the organic solvent.

14. The metallic salt electrolyte of claim 12, wherein
the organic solvent is dimethyl carbonate, diethyl carbonate, ethylmethyl carbonate, methylpropyl carbonate, ethylpropyl carbonate, methylisopropyl carbonate, dipropyl carbonate, dibutyl carbonate, propylene carbonate, ethylene carbonate, fluoroethylene carbonate, butylene carbonate, diethylene glycol dimethylether, triethylene glycol dimethylether, tetraethylene glycol dimethylether, polyethylene glycol dimethylether, dimethyl sulfone, ethylmethyl sulfone, diethyl sulfone, adiponitrile, 1,1,2,2-tetrafluoroethyl-2,2,3,3-tetrafluoropropyl ether, ethyl propionate, ethyl butyrate, benzonitrile, acetonitrile, tetrahydrofuran, 2-methyltetrahydrofuran, gamma-valerolactone, gamma-butyrolactone, succinonitrile, dioxolane, 4-methyldioxolane, N,N-dimethylformamide, N,N-dimethylacetamide, dimethylsulfoxide, dioxane, sulfolane, dichloroethane, chlorobenzene, nitrobenzene, or a combination thereof.

15. The metallic salt electrolyte of claim 1, further comprising
a lithium salt that is LiSCN, $LiN(CN)_2$, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiC_2F_5SO_3$, $LiSbF_6$, $Li(FSO_2)_2N$, $LiC_4F_9SO_3$, $LiN(SO_2CF_2CF_3)_2$, $LiSbF_6$, $LiPF_3(C_2F_5)_3$, $LiPF_3(CF_3)_3$, LiCl, LiF, LiBr, LiI, $LiB(C_2O_4)_2$, lithium difluoro(oxalato)borate, or a combination thereof.

16. The metallic salt electrolyte of claim 1, further comprising
an ionic liquid.

17. An electrochemical device comprising the metallic salt electrolyte of claim 1.

18. The electrochemical device of claim 17, wherein the electrochemical device is a lithium battery, a fuel cell, or a super capacitor.

19. A method of preparing a metallic salt electrolyte for a battery, the method comprising reacting at least one compound having a heterocyclic aromatic structure represented by one of Formulae 1H to 3H and a metallic amide salt to provide the metallic salt, wherein the metallic salt comprises a corresponding anion of the heterocyclic aromatic structure:

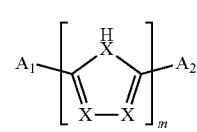

Formula 1H

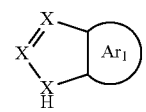

Formula 2H

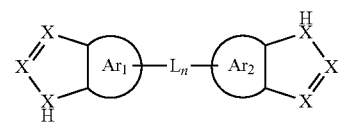

Formula 3H wherein, in Formulae 1H to 3H,
each X is independently N, P, or As,
one of $A_1$ and $A_2$ is an electron-donating group, and the other one is an electron-withdrawing group,
ring $Ar_1$ and ring $Ar_2$ are each independently an aromatic group that is a substituted or unsubstituted C6 to C24 arylene group or a substituted or unsubstituted C4 to C24 heteroarylene group, wherein the aromatic group comprises a single aromatic ring, two or more aromatic rings which are fused together, or two or more aromatic rings which are covalently connected via a single bond, —O—, —S—, —C(=O)—, —S(=O)$_2$—, —Si($R_a$)($R_b$)— wherein $R_a$ and $R_b$ are each independently a C1 to C10 alkyl group, a substituted or unsubstituted C1 to C10 alkylene group, or —C(=O)—NH—, and wherein ring $Ar_1$ and ring $Ar_2$ are each independently unsubstituted or substituted with at least one of an electron-donating group or an electron-withdrawing group,
L is a linker group, and is a single bond, —O—, —S—, —C(=O)—, —S(=O)$_2$—, —Si($R_a$)($R_b$)— wherein $R_a$ and $R_b$ are each independently a C1 to C10 alkyl group, —C(=O)—NH—, a substituted or unsubstituted C1-C12 alkylene group, a substituted or unsubstituted C2-C12 alkenylene group, a substituted or unsubstituted C2-C12 alkynylene group, a substituted or unsubstituted C6-C12 arylene group, or a substituted or unsubstituted C4-C12 heteroarylene group, wherein the linker group is unsubstituted or substituted with at least one of an electron-donating group or an electron-withdrawing group, and wherein the linker group L is uncondensed or condensed with at least one of ring $Ar_1$ or ring $Ar_2$,
m is an integer from 1 to 5, and
n is an integer from 1 to 5.

20. The method of claim 19, wherein
the metallic amide salt is a compound represented by Formula 4:

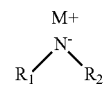

Formula 4 wherein, in Formula 4,

M$^+$ is a metallic cation that is an alkali metal cation, an alkaline earth metal cation, a transition metal cation, a post-transition metal cation, a rare earth metal cation, or a combination thereof, R$_1$ and R$_2$ are each independently a C1-C30 alkyl group, a C2-C30 alkenyl group, a C2-C30 alkynyl group, a C6-C30 aryl group, a C1-C30 alkoxy group, a C2-C30 alkoxyalkyl group, a C6-C30 aryloxy group, a C7-C30 aryloxyalkyl group, a C7-C30 arylalkyl group, a C2-C30 heteroaryl group, a C2-C30 heteroaryloxy group, a C3-C30 heteroarylalkyl group, a C4-C30 carbocyclic group, a C5-C30 carbocyclicalkyl group, a C2-C30 heterocyclic group, a C3-C30 heterocyclicalkyl group, or a C1-C30 silyl group, optionally wherein each of R$_1$ and R$_2$ is independently substituted with a C1-C30 alkyl group, a C2-C30 alkenyl group, a C2-C30 alkynyl group, a C1-C30 alkoxy group, a C2-C30 alkoxyalkyl group, a C1-C30 heteroalkyl group, a C6-C30 aryl group, a C7-C30 arylalkyl group, a C2-C30 heteroaryl group, a C3-C30 heteroarylalkyl group, a C2-C30 heteroaryloxy group, a C3-C30 heteroaryloxyalkyl group, a C6-C30 heteroarylalkoxy group, a hydroxy group, a nitro group, a cyano group, an amino group, an amidino group, a hydrazine group, a hydrazone group, a carboxyl group or a salt thereof, a sulfonyl group, a sulfamoyl group, a sulfonic acid group or salt thereof, a phosphoric acid group or salt thereof, or a combination thereof.

21. The method of claim 19, wherein
the metallic amide salt is a metallic salt of diisopropylamide, hexamethyleneamide, diisobutylamide, t-butyl-methylamide, t-butyl-trimethylsilylamide, cyclohexylisopropylamide, cyclohexylmethylamide, allyl-1-phenylethylamide, allyl-(R)-1-phenylethylamide, allyl-(S)-1-phenylethylamide, benzyl-1-phenylethylamide, benzyl-(R)-1-phenylethylamide, benzyl-(S)-1-phenylethylamide, bis-(1-phenylethyl)amide, (+)-bis-[(R)-1-phenylethyl]amide, (−)-bis-[(S)-1-phenylethyl]amide, 2,2,6,6-tentramethyl piperidide, pyrrolidide, piperidide, bis(trimethylsilyl)amide, or a combination thereof.

22. The method of claim 19, wherein
the metallic amide salt is lithium diisopropylamide, lithium bis(trimethylsilyl)amide, or a combination thereof.

23. The method of claim 19, wherein
the reacting is performed under an inert atmosphere.

24. The method of claim 19, wherein
the reacting is carried out at a temperature equal to or below 0° C.

25. The metallic salt electrolyte of claim 1, wherein the metallic cation is Li$^+$, Mg$^{2+}$, Ca$^{2+}$, Sm$^{3+}$, La$^{3+}$, Ho$^{3+}$, Sc$^{3+}$, Al$^{3+}$, Y$^{3+}$, Yb$^{3+}$, Lu$^{3+}$, Eu$^{3+}$, or a combination thereof.

* * * * *